US009017987B2

(12) United States Patent
Williamson et al.

(10) Patent No.: US 9,017,987 B2
(45) Date of Patent: Apr. 28, 2015

(54) EXPRESSION OF PROTEINS IN PLANTS

(71) Applicant: University of Cape Town, Cape Town (ZA)

(72) Inventors: Anna-Lise Williamson, Cape Town (ZA); Edward Peter Rybicki, Cape Town (ZA); James Malcolm Maclean, Cape Town (ZA); Inga Isabel Becker-Hitzeroth, Cape Town (ZA)

(73) Assignee: University of Cape Town, Cape Town (ZA)

(*) Notice: Subject to any disclaimer, the term of this patent is extended or adjusted under 35 U.S.C. 154(b) by 0 days.

(21) Appl. No.: 13/753,196

(22) Filed: Jan. 29, 2013

(65) Prior Publication Data

US 2013/0130314 A1 May 23, 2013

Related U.S. Application Data

(62) Division of application No. 11/912,912, filed as application No. PCT/ZA2006/000063 on May 2, 2006, now Pat. No. 8,535,930.

(30) Foreign Application Priority Data

Apr. 29, 2005 (ZA) ................................ 2005/03454

(51) Int. Cl.

| | |
|---|---|
| ***C12Q 1/70*** | (2006.01) |
| ***C12N 15/00*** | (2006.01) |
| ***C07K 14/11*** | (2006.01) |
| ***C12N 15/82*** | (2006.01) |
| ***C07K 14/005*** | (2006.01) |

(52) U.S. Cl.

CPC ............ *C07K 14/11* (2013.01); *C12N 15/8214* (2013.01); *C12N 15/8258* (2013.01); *C07K 14/005* (2013.01); *C12N 2760/16122* (2013.01)

(58) Field of Classification Search

None

See application file for complete search history.

(56) References Cited

U.S. PATENT DOCUMENTS

| | | | | |
|---|---|---|---|---|
| 6,156,517 | A | 12/2000 | Mayfield | |
| 7,129,391 | B1 | 10/2006 | Daniell | |
| 2004/0166121 | A1* | 8/2004 | Arntzen et al. | ............ 424/204.1 |

FOREIGN PATENT DOCUMENTS

| | | | |
|---|---|---|---|
| WO | WO 03/097673 | A | 11/2003 |
| WO | WO 2004/005467 | A | 1/2004 |
| WO | WO 2005/011367 | A | 2/2005 |

OTHER PUBLICATIONS

Varsani et al. (Virus Research, Mar. 13, 2006, vol. 120, p. 91-96).*

Treanor et al. (Vaccine, 2001, p. 1732-1737).*

Varsani et al. (Archives of Virology, 2003, vol. 148, p. 1771-1786).*

Voinnet et al. (The Plant Journal, 2003, vol. 33, p. 949-956).*

A. Varsani et al., Expression of human papillomavirus type 16 major capsid protein in transgenic *Nicotiana tabacum* c. Xanthi, *Archives of Virology*; Mar. 26, 2003; pp. 148:1771-1786.

Christopher B. Buck et al., Efficient intracellular assembelyof papillomaviral vectors; *Journal of Virology*; Jan. 2004; pp. 751-757.

Jyoti Kapila et al.., An Agrobacterium-mediated transient gene expression system for intact leaves; *Plant Science*; (1997) pp. 101-108.

Kenneth Cline et al., Import and Routing of Nucleus-Encoded Chloroplast Proteins; *Annual Reviews, Inc*., (1996), pp. 12:1-26.

Sophia Biemelt et al., Production of human papillomavirus type 16 virus-like particles in transgenic plants, *Journal of Virology*, Sep. 2003, pp. 9211-9220.

Witold Nowak et al., Effect of nuclear matrix attachment regions on transgene expression in tobacco plants, *Acta Biochimica Polonica*, Jan. 22, 2001, pp. 637-646.

Richard M. Twyman; Host plants, systems and expression strategies for molecular farming; *Molecular Farming*, (2004), pp. 191-216.

Carmen Vaquero et al., Trransient expression of a tumor-specific single-chain fragment and a chimeric antibody in tobacco leaves, *Proc. Natl. Acad. Sci. USA*, Sep. 1999, vol. 96, pp. 11128-111333.

Olivier Voinnet, RNA silencing as a plant immune system against viruses, *Trends in Genetics*, Aug. 2001, Vo. 17, No. 8, pp. 449-459.

Oliver Voinnet, et al., An enhanced transient expression system in plants based on suppression of gene silencing by the p19 protein of tomato bushy stunt virus, *The Plant Journal*, (2003), 33:949-956.

Jian Zhou et al., Identification of the Nuclear Localization Signal of Human Papillomavirus Type 16 L1 Protein, *Virology*, (1991) 185:625-632.

John Zupan et al., The transfer of DNA from *Agrobacterium tumefaciens* into plants: a feast of fundamental insights, *The Plant Journal*, (2000), 23(1):11-28.

Atsushi Takeda et al., Identification of a novel RNA silencing suppressor, NSs protein of Tomato spotted wilt virus, *Elsevier Science B.V.*, (2002), 532:75-79.

Yevgeniy Y. Studentsov et al., Enhanced Enzyme-Linked Immunosorbent Assay for Detection of Antibodies to Virus-Like Particles of Human Papillomavirus, *Journal of Clinical Microbiology*, (2002), vol. 40, No. 5, pp. 1755-1760.

(Continued)

*Primary Examiner* — Agnieszka Boesen

(74) *Attorney, Agent, or Firm* — Frommer Lawrence & Haug LLP; Ronald R. Santucci

(57) ABSTRACT

The invention relates to a method of producing an influenza virus H5 polypeptide in a plant comprising the steps of cloning an influenza H5 gene or nucleic acid encoding its functional equivalent into a vector adapted to target components present in the plant, infiltrating at least a portion of the plant with the vector or transforming plant tissue with the vector so as to transiently express the influenza virus H5 polypeptide, and/or to create a transgenic plant; and recover the influenza virus H5 polypeptide expressed by the plant. The invention further relates to vectors, transgenic plants or parts thereof and the progeny of such plants used in or which come about as a result of the method.

18 Claims, 10 Drawing Sheets

(56) References Cited

OTHER PUBLICATIONS

David A. Somers et al., Transgene integration in plants: poking or patching holes in promiscuous genomes? *Elsevier*, (2004), 15: 126-131.

Rukavtsova EB et al., Analysis of transgenic tobacco plants carrying the gene for the surface antigen of the hepatitis B virus, *Genetika*, (2003), 39(1), 51-6.

Shen Wen-Jun et al., Efficient transformation of Agrobacterium spp. by high voltage electroporation, *Biochemistry and Physiology Department*, (1989), 17:8385.

Dianna V. Pastrana et al., Reactivity of human sera in a sensitive, high-throughput pseudovirs-based papillomavirus neutralization assay for HPV16 and HPV18, *Virology*, (2004), pp. 205-216.

Sophie Pagny et al., Signals and mechanisms for protein retention in the endoplasmic reticulum, *Journal of Experimental Botany*, Feb. 1999, 50(331):157-164.

Varsani et al. (Archives of Virology, 2003, vol. 148, pp. 1771-1786, from IDS filed by Applicant in parent application on Dec. 26, 2007).

Biernelt et al. (Journal of Virology, 2003, p. 9211-9220, from IDS filed by Applicant in parent application on Dec. 26, 2007).

* cited by examiner

```
1       ATGTCCCTGT GGCTGCCCAG CGAGGCCACC GTGTACCTGC CCCCCGTGCC CGTGAGCAAG
61      GTGGTGAGCA CCGATGAGTA CGTGGCCCGG ACCAACATCT ACTACCACGC CGGCACCTCC
121     AGACTGCTGG CCGTGGGCCA CCCCTACTTC CCCATCAAGA AGCCCAACAA CAACAAGATC
181     CTGGTGCCCA AGGTGAGCGG CCTGCAATAC CGGGTGTTCA GAATCCACCT GCCCGACCCC
241     AATAAGTTCG GCTTCCCCGA CACCAGCTTC TACAACCCCG ACACCCAGAG ACTGGTGTGG
301     GCCTGCGTGG GCGTGGAGGT GGGCAGAGGC CAGCCTCTGG GCGTGGGCAT CAGCGGCCAC
361     CCTCTGCTGA ACAAGCTGGA CGACACCGAG AACGCCAGCG CCTACGCCGC CAACGCCGGC
421     GTGGATAACA GAGAATGCAT CAGCATGGAC TACAAGCAGA CCCAGCTGTG CCTCATCGGC
481     TGCAAGCCCC CCATCGGCGA GCACTGGGGC AAGGGCAGCC CCTGCACCAA CGTGGCCGTG
541     AATCCTGGCG ACTGTCCTCC CCTGGAACTC ATCAACACCG TGATCCAGGA CGGCGACATG
601     GTGGACACCG GCTTCGGCGC CATGGACTTC ACCACCCTCC AGGCCAATAA GAGCGAGGTG
661     CCCCTGGACA TCTGCACCAG CATCTGCAAG TACCCCGACT ACATCAAGAT GGTGAGCGAG
721     CCCTACGGCG ATAGCCTGTT CTTCTACCTG CGGCGGGAGC AGATGTTCGT GCGGCACCTG
781     TTCAACAGAG CCGGCACCGT GGGCGAGAAC GTGCCCGACG ACCTGTACAT CAAGGGCAGC
841     GGCAGCACCG CCAACCTGGC CAGCAGCAAC TACTTCCCTA CCCCCAGCGG CTCCATGGTG
901     ACCAGCGACG CCCAGATCTT CAACAAGCCC TACTGGCTCC AGAGAGCCCA GGGCCACAAC
961     AATGGCATCT GCTGGGGCAA CCAGCTGTTC GTGACCGTGG TGGATACCAC CCGGAGCACC
1021    AACATGTCCC TGTGCGCCGC CATCAGCACC AGCGAGACCA CCTACAAGAA CACCAACTTC
1081    AAGGAGTACC TGAGGCACGG CGAGGAGTAC GACCTCCAGT TCATCTTCCA GCTGTGCAAG
1141    ATCACCCTCA CCGCCGACGT GATGACCTAC ATCCACAGCA TGAACAGCAC CATCCTGGAG
1201    GACTGGAACT TCGGCCTGCA GCCCCCTCCT GGCGGCACCC TGGTGGAGGA GACCAGCTTC
1261    ATCGACGCCG GAGCCCCCGC ATGCCAGAAG CACACCCCTC CCGCCCCTAA GGAGGACCCC
1321    CTGAAGAAGT ACACCTTCTG GGAGGTGAAC CTGAAGGAGA AGTTCAGCGC CGACCTGGAC
1381    CAGTTCCCTC TGGGCAGAAA GTTCCTGCTG CAAGCCGGCC TGAAGGCCAA GCCTAAGTTC
1441    ACCCTGGGCA AGAGAAAGGC CACCCCCACC ACAAGCAGCA CCAGCACCAC CGCCAAGCGG
1501    AAGAAGCGCA AGCTGTGA
```

Figure 2

```
1       ATGAGCCTTT GGCTCCCTAG CGAGGCCACT GTCTACCTCC CTCCTGTCCC AGTGTCTAAG
61      GTGGTGAGCA CTGATGAGTA TGTGGCAAGG ACCAACATCT ACTACCATGC AGGAACCTCT
121     AGGCTCCTTG CAGTGGGACA CCCCTACTTC CCTATCAAGA AGCCTAACAA CAACAAGATC
181     TTGGTGCCTA AGGTGTCAGG ACTCCAATAT AGGGTGTTTA GAATCCACCT CCCTGACCCC
241     AACAAGTTTG GTTTCCCTGA CACCTCCTTC TACAACCCAG ACACCCAAAG GTTGGTGTGG
301     GCATGTGTGG GTGTGGAGGT GGGTAGGGGT CAACCATTGG GTGTGGGCAT CTCTGGCCAC
361     CCTCTCCTCA ACAAGTTGGA TGACACAGAG AATGCTTCTG CTTATGCAGC AAATGCAGGT
421     GTGGACAATA GGGAGTGCAT CTCTATGGAC TACAAGCAAA CCCAATTGTG CCTCATTGGT
481     TGCAAGCCAC CTATTGGAGA GCATTGGGGC AAGGGATCCC CATGCACTAA TGTGGCAGTG
541     AACCCAGGTG ATTGCCCACC ATTGGAGCTT ATCAACACAG TGATCCAAGA TGGTGACATG
601     GTGGACACTG GCTTTGGTGC TATGGACTTC ACTACCCTCC AAGCTAACAA GTCTGAGGTG
661     CCATTGGACA TTTGCACCTC TATTTGCAAG TACCCAGACT ACATCAAGAT GGTGTCAGAG
721     CCATATGGAG ATAGCCTCTT CTTCTACTTG AGGAGGGAGC AAATGTTTGT GAGGCACCTC
781     TTCAATAGGG CTGGTACTGT GGGTGAGAAT GTGCCAGATG ACCTCTACAT CAAGGGCTCT
841     GGATCTACTG CAAACTTGGC AAGCTCCAAC TACTTCCCTA CCCCTTCTGG TTCTATGGTG
901     ACCTCTGATG CCCAAATCTT CAACAAGCCT TATTGGCTCC AAAGGGCACA AGGCCACAAC
961     AATGGCATTT GTTGGGGTAA CCAACTCTTT GTGACTGTGG TGGACACTAC AAGGAGCACC
1021    AACATGTCCT TGTGTGCTGC CATCTCTACT TCAGAGACTA CCTACAAGAA CACTAACTTC
1081    AAGGAGTACC TTAGGCATGG AGAGGAGTAT GACCTCCAAT TCATCTTCCA ATTGTGCAAG
1141    ATCACCCTCA CTGCAGATGT GATGACCTAC ATCCACTCTA TGAACTCCAC TATCTTGGAG
1201    GATTGGAACT TTGGTCTCCA ACCTCCCCCA GGAGGCACCT TGGAGGACAC TTATAGGTTT
1261    GTGACCTCCC AAGCAATTGC TTGCCAAAAG CACACCCCTC CAGCACCTAA GGAGGACCCC
1321    CTTAAGAAGT ACACTTTTTG GGAGGTGAAC CTCAAGGAGA AGTTCTCTGC TGACTTGGAC
1381    CAATTCCCTT TGGGAAGGAA GTTCCTCCTC CAAGCAGGAC TCAAGGCCAA GCCAAAGTTC
1441    ACCTTGGGAA AGAGGAAGGC TACCCCCACC ACCTCCTCTA CCTCTACCAC TGCTAAGAGG
1501    AAGAAGAGGA AGCTCTAA
```

| | | | | | | |
|---|---|---|---|---|---|---|
| 1 | GGTACCGGAT | CCACGCGTTA | GGTCCATGGA | AAAGATCGTG | CTGCTGTTCG | CCATCGTGAG |
| 61 | CCTGGTGAAG | AGCGACCAGA | TCTGCATCGG | CTACCACGCC | AACAACAGCA | CCGAGCAGGT |
| 121 | GGACACCATC | ATGGAAAAAA | ACGTGACCGT | GACCCACGCC | CAGGACATCC | TGGAAAAGAC |
| 181 | CCACAACGGC | AAGCTGTGCG | ACCTGGACGG | CGTGAAGCCC | CTGATCCTGC | GGGACTGCAG |
| 241 | CGTGGCCGGC | TGGCTGCTGG | GCAACCCCAT | GTGCGACGAG | TTCATCAACG | TGCCCGAGTG |
| 301 | GAGCTACATC | GTGGAGAAGG | CCAACCCCGT | GAACGACCTG | TGCTACCCCG | GCGACTTCAA |
| 361 | CGACTACGAG | GAACTGAAGC | ACCTGCTGTC | CCGGATCAAC | CACTTCGAGA | AGATCCAGAT |
| 421 | CATCCCCAAG | AGCAGCTGGT | CCAGCCACGA | GGCCAGCCTG | GGCGTGAGCA | GCGCCTGCCC |
| 481 | ATACCAGGGC | AAGTCCAGCT | TCTTCCGGAA | CGTGGTGTGG | CTGATCAAGA | AGAACAGCAC |
| 541 | CTACCCCACC | ATCAAGCGGA | GCTACAACAA | CACCAACCAG | GAAGATCTGC | TGGTCCTGTG |
| 601 | GGGCATCCAC | CACCCCAACG | ACGCCGCCGA | GCAGACCAAG | CTGTACCAGA | ACCCCACCAC |
| 661 | CTACATCAGC | GTGGGCACCA | GCACCCTGAA | CCAGCGGCTG | GTGCCCCGGA | TCGCCACCCG |
| 721 | GTCCAAGGTG | AACGGCCAGA | GCGGCCGGAT | GGAATTTTTC | TGGACCATCC | TGAAGCCCAA |
| 781 | CGATGCCATC | AACTTCGAGA | GCAACGGCAA | CTTCATCGCC | CCCGAGTACG | CCTACAAGAT |
| 841 | CGTGAAGAAG | GGCGACAGCA | CCATCATGAA | GAGCGAGCTG | GAATACGGCA | ACTGCAACAC |
| 901 | CAAGTGCCAG | ACCCCTATGG | GCGCCATCAA | CAGCAGCATG | CCCTTCCACA | ACATCCACCC |
| 961 | CCTGACCATC | GGCGAGTGCC | CCAAGTACGT | GAAGAGCAAC | AGGCTGGTGC | TGGCCACCGG |
| 1021 | CCTGCGGAAC | AGCCCCCAGC | GGGAGCGGCG | GAGGAAGAAG | CGGGGCCTGT | TCGGCGCCAT |
| 1081 | CGCCGGCTTC | ATCGAGGGCG | GCTGGCAGGG | CATGGTGGAC | GGGTGGTACG | GCTACCACCA |
| 1141 | CAGCAATGAG | CAGGGCAGCG | GCTACGCCGC | CGACAAAGAG | AGCACCCAGA | AGGCCATCGA |
| 1201 | CGGCGTCACC | AACAAGGTGA | ACAGCATCAT | CGACAAGATG | AACACCCAGT | TCGAGGCCGT |
| 1261 | GGGCCGGGAG | TTCAACAACC | TGGAACGGCG | GATCGAGAAC | CTGAACAAGA | AAATGGAAGA |
| 1321 | TGGCTTCCTG | GACGTGTGGA | CCTACAACGC | CGAGCTGCTG | GTGCTGATGG | AAAACGAGCG |
| 1381 | GACCCTGGAC | TTCCACGACA | GCAACGTGAA | GAACCTGTAC | GACAAAGTGC | GGCTGCAGCT |
| 1441 | GCGGGACAAC | GCCAAAGAGC | TGGGCAACGG | CTGCTTCGAG | TTCTACCACA | AGTGCGACAA |
| 1501 | CGAGTGCATG | GAAAGCGTGC | GGAACGGCAC | CTACGACTAC | CCCCAGTACA | GCGAGGAAGC |
| 1561 | CCGGCTGAAG | CGGGAGGAAA | TCAGCGGCGT | GAAACTGGAA | AGCATCGGCA | TCTACCAGAT |
| 1621 | CCTGAGCATC | TACAGCACCG | TGGCCAGCAG | CCTGGCCCTG | GCCATCATGG | TGGCCGGCCT |
| 1681 | GAGCCTGTGG | ATGTGCAGCA | ACGGCAGCCT | GCAGTGTAGA | GCGGCCGCAT | AATCTAGAGA |
| 1741 | GCTC | | | | | |

```
1       GGTACCGGAT CCACGCGTTA GGTCCATGGA AAAGATCGTG CTGCTGTTCG CCATCGTGAG
61      CCTGGTGAAG AGCGACCAGA TCTGCATCGG CTACCACGCC AACAACAGCA CCGAGCAGGT
121     GGACACCATC ATGGAAAAAA ACGTGACCGT GACCCACGCC CAGGACATCC TGGAAAAGAC
181     CCACAACGGC AAGCTGTGCG ACCTGGACGG CGTGAAGCCC CTGATCCTGC GGGACTGCAG
241     CGTGGCCGGC TGGCTGCTGG GCAACCCCAT GTGCGACGAG TTCATCAACG TGCCCGAGTG
301     GAGCTACATC GTGGAGAAGG CCAACCCCGT GAACGACCTG TGCTACCCCG GCGACTTCAA
361     CGACTACGAG GAACTGAAGC ACCTGCTGTC CCGGATCAAC CACTTCGAGA AGATCCAGAT
421     CATCCCCAAG AGCAGCTGGT CCAGCCACGA GGCCAGCCTG GGCGTGAGCA GCGCCTGCCC
481     ATACCAGGGC AAGTCCAGCT TCTTCCGGAA CGTGGTGTGG CTGATCAAGA AGAACAGCAC
541     CTACCCCACC ATCAAGCGGA GCTACAACAA CACCAACCAG GAAGATCTGC TGGTCCTGTG
601     GGGCATCCAC CACCCCAACG ACGCCGCCGA GCAGACCAAG CTGTACCAGA ACCCCACCAC
661     CTACATCAGC GTGGGCACCA GCACCCTGAA CCAGCGGCTG GTGCCCCGGA TCGCCACCCG
721     GTCCAAGGTG AACGGCCAGA GCGGCCGGAT GGAATTTTTC TGGACCATCC TGAAGCCCAA
781     CGATGCCATC AACTTCGAGA GCAACGGCAA CTTCATCGCC CCCGAGTACG CCTACAAGAT
841     CGTGAAGAAG GGCGACAGCA CCATCATGAA GAGCGAGCTG GAATACGGCA ACTGCAACAC
901     CAAGTGCCAG ACCCCTATGG GCGCCATCAA CAGCAGCATG CCCTTCCACA ACATCCACCC
961     CCTGACCATC GGCGAGTGCC CCAAGTACGT GAAGAGCAAC AGGCTGGTGC TGGCCACCGG
1021    CCTGCGGAAC AGCCCCCAGC GGGAGCGGCG GAGGAAGAAG CGGGGCCTGT TCGGCGCCAT
1081    CGCCGGCTTC ATCGAGGGCG GCTGGCAGGG CATGGTGGAC GGGTGGTACG GCTACCACCA
1141    CAGCAATGAG CAGGGCAGCG GCTACGCCGC CGACAAAGAG AGCACCCAGA AGGCCATCGA
1201    CGGCGTCACC AACAAGGTGA ACAGCATCAT CGACAAGATG AACACCCAGT TCGAGGCCGT
1261    GGGCCGGGAG TTCAACAACC TGGAACGGCG GATCGAGAAC CTGAACAAGA AAATGGAAGA
1321    TGGCTTCCTG GACGTGTGGA CCTACAACGC CGAGCTGCTG GTGCTGATGG AAAACGAGCG
1381    GACCCTGGAC TTCCACGACA GCAACGTGAA GAACCTGTAC GACAAAGTGC GGCTGCAGCT
1441    GCGGGACAAC GCCAAAGAGC TGGGCAACGG CTGCTTCGAG TTCTACCACA AGTGCGACAA
1501    CGAGTGCATG GAAAGCGTGC GGAACGGCAC CTACGACTAC CCCCAGTACA GCGAGGAAGC
1561    CCGGCTGAAG CGGGAGGAAA TCAGCGGCGT GAAACTGGAA AGCATCGGCA TCTACCAGAT
1621    CATGTGCAGC AACGGCAGCC TGCAGTGTAG AGCGGCCGCA TAATCTAGAG AGCTC
```

Figure 11

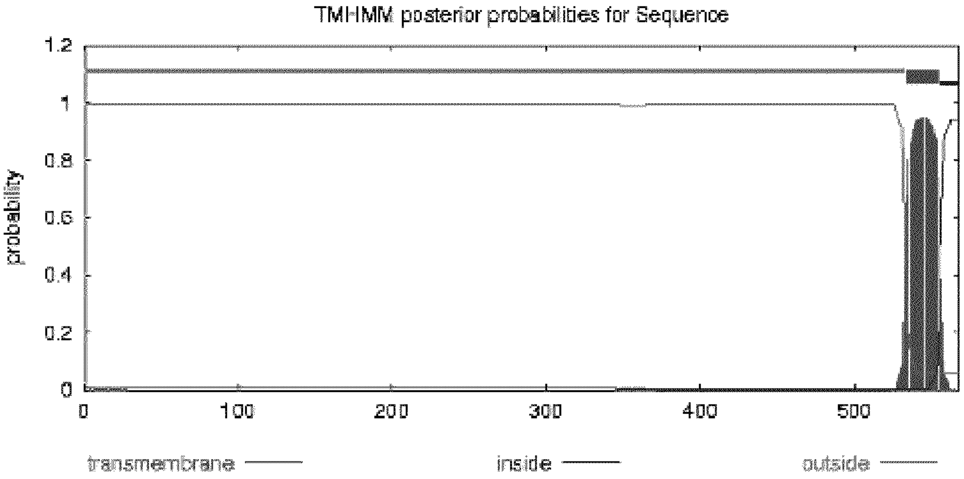

Figure 12

SEQUENCE LISTING

<160> NUMBER OF SEQ ID NOS: 16

<210> SEQ ID NO 1
<211> LENGTH: 33
<212> TYPE: DNA
<213> ORGANISM: Artificial
<220> FEATURE:
<223> OTHER INFORMATION: Primer

<400> SEQUENCE: 1
ggacgcgtta ggtacatgtc tctttggctg cct 33

<210> SEQ ID NO 2
<211> LENGTH: 36
<212> TYPE: DNA
<213> ORGANISM: Artificial
<220> FEATURE:

-continued

<223> OTHER INFORMATION: Primer

<400> SEQUENCE: 2
tctagactcg agttacagct tacgtttttt gcgttt 36

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
agcggccgcc agcttacgtt ttttgcg 27

<210> SEQ ID NO 4
<211> LENGTH: 33
<212> TYPE: DNA
<213> ORGANISM: Artificial
<220> FEATURE:
<223> OTHER INFORMATION: Primer

<400> SEQUENCE: 4
ggacgcgtga gattcatgag cctttggctc cct 33

<210> SEQ ID NO 5
<211> LENGTH: 37
<212> TYPE: DNA
<213> ORGANISM: Artificial
<220> FEATURE:
<223> OTHER INFORMATION: Primer

<400> SEQUENCE: 5
atctagactc gagttagagc ttcctcttct tcctctt 37

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
agcggccgcg agcttcctct tcttcctctt 30

<210> SEQ ID NO 7
<211> LENGTH: 33
<212> TYPE: DNA
<213> ORGANISM: Artificial
<220> FEATURE:
<223> OTHER INFORMATION: Primer

<400> SEQUENCE: 7
ggacgcgtga ggttcatgag cctgtggctg ccc 33

<210> SEQ ID NO 8
<211> LENGTH: 34
<212> TYPE: DNA
<213> ORGANISM: Artificial
<220> FEATURE:
<223> OTHER INFORMATION: Primer

<400> SEQUENCE: 8
atctagactc gagtcacagc ttgcgcttct tccg 34

<210> SEQ ID NO 9
<211> LENGTH: 28
<212> TYPE: DNA
<213> ORGANISM: Artificial
<220> FEATURE:
<223> OTHER INFORMATION: Primer

<400> SEQUENCE: 9
agcggccgcc agcttgcgct tcttccgc 28

<210> SEQ ID NO 10
<211> LENGTH: 33
<212> TYPE: DNA
<213> ORGANISM: Artificial
<220> FEATURE:
<223> OTHER INFORMATION: Primer

<400> SEQUENCE: 10
tctagactcg agtcagccca gggtgaactt agg 33

<210> SEQ ID NO 11
<211> LENGTH: 34
<212> TYPE: DNA
<213> ORGANISM: Artificial
<220> FEATURE:
<223> OTHER INFORMATION: Primer

<400> SEQUENCE: 11
ggacgcgtta ggtccatggc tagcaaagga gaag 34

<210> SEQ ID NO 12
<211> LENGTH: 29
<212> TYPE: DNA
<213> ORGANISM: Artificial
<220> FEATURE:
<223> OTHER INFORMATION: Primer

<400> SEQUENCE: 12
atctagatta tttgtagagc tcatccatg 29

<210> SEQ ID NO 13
<211> LENGTH: 1518
<212> TYPE: DNA
<213> ORGANISM: Human papillomavirus type 16

<400> SEQUENCE: 13
atgtccctgt ggctgcccag cgaggccacc gtgtacctgc cccccgtgcc cgtgagcaag 60
gtggtgagca ccgatgagta cgtggcccgg accaacatct actaccacgc cggcacctcc 120
agactgctgg ccgtgggcca cccctacttc cccatcaaga agcccaacaa caacaagatc 180
ctggtgccca aggtgagcgg cctgcaatac cgggtgttca gaatccacct gcccgacccc 240
aataagttcg gcttccccga caccagcttc tacaaccccg acacccagag actggtgtgg 300
gcctgcgtgg gcgtggaggt gggcagaggc cagcctctgg gcgtgggcat cagcggccac 360
cctctgctga acaagctgga cgacaccgag aacgccagcg cctacgccgc caacgccggc 420
gtggataaca gagaatgcat cagcatggac tacaagcaga cccagctgtg cctcatcggc 480
tgcaagcccc ccatcggcga gcactggggc aagggcagcc cctgcaccaa cgtggccgtg 540
aatcctggcg actgtcctcc cctggaactc atcaacaccg tgatccagga cggcgacatg 600
gtggacaccg gcttcggcgc catggacttc accaccctcc aggccaataa gagcgaggtg 660
cccctggaca tctgcaccag catctgcaag taccccgact acatcaagat ggtgagcgag 720

-continued

```
ccctacggcg atagcctgtt cttctacctg cggcgggagc agatgttcgt gcggcacctg    780

ttcaacagag ccggcaccgt gggcgagaac gtgcccgacg acctgtacat caagggcagc    840

ggcagcaccg ccaacctggc cagcagcaac tacttcccta cccccagcgg ctccatggtg    900

accagcgacg cccagatctt caacaagccc tactggctcc agagagccca gggccacaac    960

aatggcatct gctggggcaa ccagctgttc gtgaccgtgg tggataccac ccggagcacc   1020

aacatgtccc tgtgcgccgc catcagcacc agcgagacca cctacaagaa caccaacttc   1080

aaggagtacc tgaggcacgg cgaggagtac gacctccagt tcatcttcca gctgtgcaag   1140

atcaccctca ccgccgacgt gatgacctac atccacagca tgaacagcac catcctggag   1200

gactggaact tcggcctgca gcccccctcct ggcggcaccc tggtggagga gaccagcttc   1260

atcgacgccg gagcccccgc atgccagaag cacacccctc ccgcccctaa ggaggacccc   1320

ctgaagaagt acaccttctg ggaggtgaac ctgaaggaga agttcagcgc cgacctggac   1380

cagttccctc tgggcagaaa gttcctgctg caagccggcc tgaaggccaa gcctaagttc   1440

accctgggca agagaaaggc cacccccacc acaagcagca ccagcaccac cgccaagcgg   1500

aagaagcgca agctgtga                                                 1518
```

```
<210> SEQ ID NO 14
<211> LENGTH: 1518
<212> TYPE: DNA
<213> ORGANISM: Human papillomavirus type 16

<400> SEQUENCE: 14
```

```
atgagccttt ggctccctag cgaggccact gtctacctcc ctcctgtccc agtgtctaag     60

gtggtgagca ctgatgagta tgtggcaagg accaacatct actaccatgc aggaacctct    120

aggctccttg cagtgggaca cccctacttc cctatcaaga agcctaacaa caacaagatc    180

ttggtgccta aggtgtcagg actccaatat agggtgttta gaatccacct ccctgacccc    240

aacaagtttg gtttccctga cacctccttc tacaacccag acacccaaag gttggtgtgg    300

gcatgtgtgg gtgtggaggt gggtaggggt caaccattgg gtgtgggcat ctctggccac    360

cctctcctca acaagttgga tgacacagag aatgcttctg cttatgcagc aaatgcaggt    420

gtggacaata gggagtgcat ctctatggac tacaagcaaa cccaattgtg cctcattggt    480

tgcaagccac ctattggaga gcattggggc aagggatccc catgcactaa tgtggcagtg    540

aacccaggtg attgcccacc attggagctt atcaacacag tgatccaaga tggtgacatg    600

gtggacactg gctttggtgc tatggacttc actaccctcc aagctaacaa gtctgaggtg    660

ccattggaca tttgcacctc tatttgcaag tacccagact acatcaagat ggtgtcagag    720

ccatatggag atagcctctt cttctacttg aggagggagc aaatgtttgt gaggcacctc    780

ttcaataggg ctggtactgt gggtgagaat gtgccagatg acctctacat caagggctct    840

ggatctactg caaacttggc aagctccaac tacttcccta ccccttctgg ttctatggtg    900

acctctgatg cccaaatctt caacaagcct tattggctcc aaagggcaca aggccacaac    960

aatggcattt gttggggtaa ccaactcttt gtgactgtgg tggacactac aaggagcacc   1020

aacatgtcct tgtgtgctgc catctctact tcagagacta cctacaagaa cactaacttc   1080

aaggagtacc ttaggcatgg agaggagtat gacctccaat tcatcttcca attgtgcaag   1140

atcaccctca ctgcagatgt gatgacctac atccactcta tgaactccac tatcttggag   1200

gattggaact ttggtctcca acctccccca ggaggcacct tggaggacac ttataggttt   1260

gtgacctccc aagcaattgc ttgccaaaag cacacccctc cagcacctaa ggaggacccc   1320
```

-continued cttaagaagt acactttttg ggaggtgaac ctcaaggaga agttctctgc tgacttggac 1380
caattccctt tgggaaggaa gttcctcctc caagcaggac tcaaggccaa gccaaagttc 1440
accttgggaa agaggaaggc tacccccacc acctcctcta cctctaccac tgctaagagg 1500
aagaagagga agctctaa 1518

<210> SEQ ID NO 15
<211> LENGTH: 1744
<212> TYPE: DNA
<213> ORGANISM: Influenza A virus

<400> SEQUENCE: 15
ggtaccggat ccacgcgtta ggtccatgga aaagatcgtg ctgctgttcg ccatcgtgag 60
cctggtgaag agcgaccaga tctgcatcgg ctaccacgcc aacaacagca ccgagcaggt 120
ggacaccatc atggaaaaaa acgtgaccgt gacccacgcc caggacatcc tggaaaagac 180
ccacaacggc aagctgtgcg acctggacgg cgtgaagccc ctgatcctgc gggactgcag 240
cgtggccggc tggctgctgg gcaaccccat gtgcgacgag ttcatcaacg tgcccgagtg 300
gagctacatc gtggagaagg ccaaccccgt gaacgacctg tgctaccccg gcgacttcaa 360
cgactacgag gaactgaagc acctgctgtc ccggatcaac cacttcgaga agatccagat 420
catccccaag agcagctggt ccagccacga ggccagcctg ggcgtgagca gcgcctgccc 480
ataccagggc aagtccagct tcttccggaa cgtggtgtgg ctgatcaaga agaacagcac 540
ctaccccacc atcaagcgga gctacaacaa caccaaccag gaagatctgc tggtcctgtg 600
gggcatccac caccccaacg acgccgccga gcagaccaag ctgtaccaga accccaccac 660
ctacatcagc gtgggcacca gcaccctgaa ccagcggctg gtgccccgga tcgccacccg 720
gtccaaggtg aacggccaga gcggccggat ggaatttttc tggaccatcc tgaagcccaa 780
cgatgccatc aacttcgaga gcaacggcaa cttcatcgcc cccgagtacg cctacaagat 840
cgtgaagaag ggcgacagca ccatcatgaa gagcgagctg gaatacggca actgcaacac 900
caagtgccag acccctatgg gcgccatcaa cagcagcatg cccttccaca acatccaccc 960
cctgaccatc ggcgagtgcc ccaagtacgt gaagagcaac aggctggtgc tggccaccgg 1020
cctgcggaac agcccccagc gggagcggcg gaggaagaag cggggcctgt tcggcgccat 1080
cgccggcttc atcgagggcg gctggcaggg catggtggac gggtggtacg gctaccacca 1140
cagcaatgag cagggcagcg gctacgccgc cgacaaagag agcacccaga aggccatcga 1200
cggcgtcacc aacaaggtga acagcatcat cgacaagatg aacacccagt tcgaggccgt 1260
gggccgggag ttcaacaacc tggaacggcg gatcgagaac ctgaacaaga aaatggaaga 1320
tggcttcctg gacgtgtgga cctacaacgc cgagctgctg gtgctgatgg aaaacgagcg 1380
gaccctggac ttccacgaca gcaacgtgaa gaacctgtac gacaaagtgc ggctgcagct 1440
gcgggacaac gccaaagagc tgggcaacgg ctgcttcgag ttctaccaca agtgcgacaa 1500
cgagtgcatg gaaagcgtgc ggaacggcac ctacgactac ccccagtaca gcgaggaagc 1560
ccggctgaag cgggaggaaa tcagcggcgt gaaactggaa agcatcggca tctaccagat 1620
cctgagcatc tacagcaccg tggccagcag cctggccctg gccatcatgg tggccggcct 1680
gagcctgtgg atgtgcagca acggcagcct gcagtgtaga gcggccgcat aatctagaga 1740
gctc 1744

<210> SEQ ID NO 16

-continued

```
<211> LENGTH: 1675
<212> TYPE: DNA
<213> ORGANISM: Influenza A virus

<400> SEQUENCE: 16

ggtaccggat ccacgcgtta ggtccatgga aaagatcgtg ctgctgttcg ccatcgtgag     60

cctggtgaag agcgaccaga tctgcatcgg ctaccacgcc aacaacagca ccgagcaggt    120

ggacaccatc atggaaaaaa acgtgaccgt gacccacgcc caggacatcc tggaaaagac    180

ccacaacggc aagctgtgcg acctggacgg cgtgaagccc ctgatcctgc gggactgcag    240

cgtggccggc tggctgctgg gcaaccccat gtgcgacgag ttcatcaacg tgcccgagtg    300

gagctacatc gtggagaagg ccaaccccgt gaacgacctg tgctaccccg gcgacttcaa    360

cgactacgag gaactgaagc acctgctgtc ccggatcaac cacttcgaga agatccagat    420

catccccaag agcagctggt ccagccacga ggccagcctg ggcgtgagca gcgcctgccc    480

ataccagggc aagtccagct tcttccggaa cgtggtgtgg ctgatcaaga agaacagcac    540

ctaccccacc atcaagcgga gctacaacaa caccaaccag gaagatctgc tggtcctgtg    600

gggcatccac caccccaacg acgccgccga gcagaccaag ctgtaccaga accccaccac    660

ctacatcagc gtgggcacca gcaccctgaa ccagcggctg gtgccccgga tcgccacccg    720

gtccaaggtg aacggccaga gcggccggat ggaatttttc tggaccatcc tgaagcccaa    780

cgatgccatc aacttcgaga gcaacggcaa cttcatcgcc cccgagtacg cctacaagat    840

cgtgaagaag ggcgacagca ccatcatgaa gagcgagctg gaatacggca actgcaacac    900

caagtgccag acccctatgg gcgccatcaa cagcagcatg cccttccaca acatccaccc    960

cctgaccatc ggcgagtgcc ccaagtacgt gaagagcaac aggctggtgc tggccaccgg   1020

cctgcggaac agcccccagc gggagcggcg gaggaagaag cggggcctgt tcggcgccat   1080

cgccggcttc atcgagggcg gctggcaggg catggtggac gggtggtacg gctaccacca   1140

cagcaatgag cagggcagcg gctacgccgc cgacaaagag agcacccaga aggccatcga   1200

cggcgtcacc aacaaggtga acagcatcat cgacaagatg aacacccagt tcgaggccgt   1260

gggccgggag ttcaacaacc tggaacggcg gatcgagaac ctgaacaaga aaatggaaga   1320

tggcttcctg gacgtgtgga cctacaacgc cgagctgctg gtgctgatgg aaaacgagcg   1380

gaccctggac ttccacgaca gcaacgtgaa gaacctgtac gacaaagtgc ggctgcagct   1440

gcgggacaac gccaaagagc tgggcaacgg ctgcttcgag ttctaccaca agtgcgacaa   1500

cgagtgcatg gaaagcgtgc ggaacggcac ctacgactac ccccagtaca gcgaggaagc   1560

ccggctgaag cgggaggaaa tcagcggcgt gaaactggaa agcatcggca tctaccagat   1620

catgtgcagc aacggcagcc tgcagtgtag agcggccgca taatctagag agctc        1675
```

EXPRESSION OF PROTEINS IN PLANTS

This application is a division of U.S. patent application Ser. No. 11/912,912 filed Apr. 30, 2008 entitled "Expression of Proteins in Plants" which is a 371 filing of PCT/ZA2006/000063 filed on May 2, 2006, published on Nov. 9, 2006 under publication number WO 2006/119516 A2 which claims priority benefits from South African Patent Application Number 2005/03454 filed Apr. 29, 2005, the disclosures of which are all hereby incorporated by reference.

BACKGROUND TO THE INVENTION

This invention relates to the expression of protein in plants. In particular, this invention relates to a method of transgenic protein expression and intracellular localisation for high yield protein production. This invention also relates to the production of human papillomavirus (HPV) protein and/or influenza virus H5 protein in a plant. This invention further relates to a rapid mechanism for evaluating protein expression within plants.

The use of transgenic plants for the large-scale production of heterologous proteins is gradually gaining widespread acceptance, and could be a platform for the cost-effective production of vaccine proteins. The generation of transgenic plants to investigate the expression characteristics of a large assortment of proteins and/or expression vectors is not always viable due to the time-consuming nature of this process. In contrast, transient expression systems are capable of rapidly evaluating protein expression of a variety of different proteins in a variety of plant species.

Another problem relating to the use of transgenic plants for large-scale production of proteins is the generally disappointingly low levels of heterologous protein produced. Plant plastids, especially the chloroplast, have successfully been transformed with recombinant vectors expressing heterologous protein to significantly increase the levels of protein produced per total soluble protein in the plant (see, for example, WO2005/011367 and WO2004/005467A2). Plastids are also able to import a variety of molecules, including proteins. There are different processes through which this occurs, one of which involves interaction with the thylakoid membrane of the plastid. Targeting of heterologous proteins to the plastid is a mechanism of significantly increasing protein accumulation within the plant cell.

*Agrobacterium*-mediated gene transfer has been utilised for many years to generate stably transformed plants. This method involves the transfer of the T-complex (a complex formed with the agrobacterial T-DNA and virulence gene products) from *Agrobacterium* strains to plant cells (Zupan et al., 2000). Any DNA located between the 25 bp direct repeats (left and right borders) that delimit the single-stranded T-DNA is transferred into the plant cell nucleus (Zupan et al., 2000), where it integrates into the plant chromosome via illegitimate recombination (Somers and Makarevitch, 2004). Many of the T-DNA copies present in the nucleus do not integrate, but get transcribed, causing transient expression. Transient expression is not affected by the position effect, and can produce dramatically higher foreign protein levels than stable transformation (Kapila et al., 1997).

Two *Agrobacterium* infiltration (agroinfiltation) methods are commonly utilised: Injection and vacuum infiltration. *Agrobacterium* injection involves direct injection into the abaxial airspaces of a leaf, while the leaf is still attached to the plant (Voinnet et al., 2003). During vacuum infiltration a vacuum is applied to an agrobacterial suspension in which leaves are submerged (Kapila et al., 1997). Although usually performed on just a few leaves, this technique can be scaled up: Researchers at *Medicago* Inc. (Quebec, Canada) are able to agroinfiltrate up to 7500 alfalfa leaves per week, and Stefan Schillberg and colleagues (Institute for Molecular Biotechnology, RWTH Aachen, Germany) have agroinfiltrated up to 100 kg of tobacco leaves (Twyman 2004).

*Agrobacterium*-mediated transient expression peaks 60 to 72 hours post infiltration, and then declines sharply as a result of post-transcriptional gene silencing (PTGS) (Voinnet et al., 2003). PTGS or RNA interference is an adaptive antiviral defence response that limits virus replication and spread in plants. This process involves recognition of a target RNA and initiation of a sequence-specific RNA degradation pathway in the cytoplasm (Voinnet, 2001). Certain plant viruses encode silencing suppressors that have the ability to inhibit PTGS. Some of these silencing suppressors proteins, such as NSs of the tomato spotted wilt virus (TSWV) (Takeda et al., 2002), and p19 of tomato bushy stunt virus (Voinnet et al., 2003) have been utilised to prolong and amplify *Agrobacterium*-mediated transient expression by the co-infiltration of *Agrobacterium* containing a silencing suppressor gene.

A need exists to optimise the expression of commercially viable proteins in plants to levels that would make plants a viable platform. In particular, a need exists for a method of producing HPV protein and/or influenza virus H5 protein in a plant.

Further needs exist for vectors, transgenic plants or parts thereof and the progeny of such plants to effect the need as hereinbefore described.

SUMMARY OF THE INVENTION

According to a first aspect to the present invention there is provided a method of producing a HPV polypeptides and/or an influenza virus H5 polypeptide in a plant comprising the steps of:

1. cloning a HPV gene and/or an influenza virus H5 gene or nucleic acid encoding their functional equivalents into a vector adapted to target components present in the plant;
2. infiltrating at least a portion of the plant with the vector or transforming plant tissue with the vector so as to transiently express the HPV polypeptides and/or an influenza virus H5 polypeptide, and/or to create a transgenic plant; and
3. recovering the HPV polypeptides and/or an influenza virus H5 polypeptide expressed by the plant.

The term 'plant' is intended to encompass all living organisms which lack specialised sense organs and the power of voluntary movement. As such, the definition includes both monocotyledons and dicotyledons and all photosynthetic organisms.

The term 'HPV polypeptides' is intended to encompass HPV L1 protein; a chimaeric HPV L1 peptide fused to another HPV antigen peptide; a chimaeric HPV L1 peptide fused to a heterologous peptide derived from any antigenic epitope, B-cell or T-cell specific and a HPV L2 protein or their functional equivalents. The same applies, mutatis mutandis to the term 'HPV gene'.

The term 'plant components' is intended to encompass plastids, endoplasmic reticuli, cytoplasm and apoplasts. Preferably the plant component is a plastid.

By targeting it is intended that targeting sequences may be included in the vector. Such targeting sequences may be translated into a peptide which directs the vector or product thereof to the desired component in the plant, such as a plastid.

The vector according to the present invention preferably includes promoters and other necessary regulators such as terminators or the like operably linked to the coding sequence.

It will be appreciated that infiltrating at least a portion of the plant with the vector may give rise to transient expression of the protein and transforming plant tissue with the vector so as to create a transgenic plant may give rise to transgenic expression of the protein, both of which forms of expression are contemplated to fall within the ambit of the present application.

In this specification reference to a protein, peptide or a gene or their functional equivalents includes references to variants thereof which are capable of performing largely the same function as the protein, peptide, polypeptide or gene. Preferably this invention relates to the production of the HPV-16 L1 protein; a chimaeric HPV L1 peptide fused to another HPV antigen peptide; a chimaeric HPV L1 peptide fused to a heterologous peptide derived from any antigenic epitope, B-cell or T-cell specific; a HPV L2 protein; or an influenza virus H5 protein.

Preferably the vectors are binary vectors, more preferable *Agrobacterium tumefaciens* binary vectors.

The vector may be adapted to target plastids by causing an expressed polypeptide to include a portion capable of interacting with the thylakoid membranes of the plastids, in particular the transfer mechanism of the thylakoid membranes. This interaction may cause the polypeptide to be imported into the plastid from the cytoplasm where it is expressed. The mechanism of importation into the cytoplasm may be important for proper folding of the proteins.

However, it will be appreciated that the vector may be adapted to target the plastids themselves to become transformed and expression of the polypeptide may occur wholly within the plastid.

Without wishing to be bound by theory, the applicant is of the view that a polypeptide imported into the plastid is imported in its primary structure and undergoes folding into its secondary and tertiary structure within the plastid, i.e. remote from the cytoplasm of the cell. As such, the applicant regards it as a logical extension of the inventive principal that expression of the polypeptide by the vector may occur within the plastid, whereupon it then adopts its secondary and tertiary structures. In other words, the applicants consider the inventive principle to extend to transformation of the plastids. Under such conditions expression of the protein would occur entirely within the plastid and without contact with the cytoplasm of the cell.

Preferably the HPV L1 gene; chimaeric HPV L1 gene fused to another HPV antigen gene; chimaeric HPV L1 gene fused to a heterologous gene derived from any antigenic epitope, B-cell or T-cell specific; HPV L2 gene; or influenza virus H5 gene is an optimized gene, for example, human-codon optimized, BCG-codon optimized or plant-codon optimized. The HPV L1 gene or genes of the HPV L1 chimeras may also be modified in another manner, for example nuclear localization signal deficient.

The method according to the present invention may further include the step of co-infiltration of the plant with a suppressor protein adapted to inhibit post-transcriptional gene silencing in a plant. Preferably the suppressor protein is the NSs protein of the tomato spotted wilt virus or the p19 of tomato bushy stunt virus. Most preferably the suppressor protein is NSs.

In a preferred embodiment of the present invention the plastids are selected from chloroplasts, chromoplasts and leucoplasts. The plastids are preferably chloroplasts.

The infiltration can be done by direct injection or by vacuum. According to one aspect of the present invention, whole plants may be vacuum infiltrated. In this specification, ‘whole plants’ should be considered to include its plants which have had their roots removed as well as plants which have been partially defoliated as well as largely intact plants. Reference to plant should include reference to plant parts including but not limited to seed, leaf, root, stem, flower, fruit, embryo, meristem, hypocotyl, epicotyl, cotyledon, pollen and tissue.

In the method according to the present invention, both infiltration and transformation of the plant may be achieved with *Agrobacterium tumefaciens* which has been transformed to accept the vector.

The plant may also be selected from *Nicotiana benthamiana* and *N. tabacum*. It will be appreciated, however, that any plant which supports transient protein expression or being made transgenic will be suitable for the purposes of the present invention.

Infiltration is preferably performed upon the leaves of the plant. Direct injection infiltration is preferably performed on the abaxial region of the leaf.

According to a second aspect to the present invention there is provided a method of producing HPV polypeptide and/or an influenza virus H5 polypeptide in a plant wherein substantially the whole plant is infiltrated with a suitable vector by means of vacuum infiltration.

According to a third aspect to the present invention there is provided a HPV polypeptide and/or an influenza virus H5 polypeptide whenever produced according to a method as hereinbefore described.

According to the fourth aspect to the present invention there is provided use of a vector into which a HPV gene and/or an influenza virus H5 gene has been cloned, which vector is adapted to target components present in a plant, to produce a transgenic plant capable of expressing HPV polypeptides and/or an influenza virus H5 polypeptides.

According to a fifth aspect to the present invention there is provided a vector into which a HPV gene and/or an influenza virus H5 gene has been cloned, which vector is adapted to target components present in a plant, to produce a transgenic plant capable of expressing HPV polypeptides and/or an influenza virus H5 polypeptides.

According to a sixth aspect to the present invention there is provided a prophylactic or therapeutic vaccine consisting of HPV polypeptide or an influenza virus H5 polypeptide capable of inducing an immunogenic response in a suitable host, whenever produced by a method as hereinbefore described.

According to an seventh aspect to the present invention there is provided a transgenic plant, part or progeny thereof containing a cell capable of expressing a HPV polypeptide and/or an influenza virus H5 polypeptide.

In these subsequent aspects to the invention, the options and preferences of the first aspect apply mutatis mutandis.

A need existed to optimise the expression of commercially viable proteins in plants, to levels that would make plants a viable platform. One example is the production of HPV L1 major capsid protein as capsomeres and/or as virus-like particles (VLPs) for human vaccine or reagent purposes.

By following the teaching of this invention, the expression of a number of antigenic proteins can be compared, as well as the effect of plant cell compartment targeting of the proteins by transient expression by means of agroinfiltration. This method involves the infiltration of *Agrobacterium tumefaciens* recombinants carrying expression vectors into plants by direct injection or by creating a vacuum over leaves submerged or soaked in the *Agrobacterium* culture.

Human-codon optimised or BCG codon optimised HPV L1 was expressed at significantly higher levels than the other L1 sequences and human codon optimisation has also resulted in high expression of influenza H5 protein. Chloroplast-targeting caused significantly higher accumulation than cytoplasmic or endoplasmic reticulum (ER)-targeting. Electron microscopy of whole-plant extracts of HPV L1 revealed that L1 was assembling into virus-like particles (VLPs) in the plants. The protein produced also reacted with appropriate HPV L1-specific monoclonal antibodies (MAbs) which recognise conformation-specific epitopes.

L1 obtained by transient expression in plants induced high levels of L1-specific antibodies in mice, and these antibodies were found to be neutralising in an in vitro neutralisation assay.

The expression vectors that facilitated high transient L1 expression in plant chloroplasts were utilised to generate transgenic plants that also expressed high levels of the other polypeptides as hereinbefore described.

*Agrobacterium* vacuum infiltration typically involves infiltration of leaves that have been removed from the stem. The present invention describes novel vacuum infiltration of intact plants, or intact rootless plants. Intact plants with small root systems can removed from the soil, infiltrated and replanted without loss of viability. Large root systems can be removed, the plant infiltrated, and then replanted in plant foam to be cultured for at least three days without loss of viability. Plants with complex root systems can also be grown hydroponically which permits infiltration without root removal. Whole plants are easier to incubate than loose leaves after the infiltration process, and they survive for longer, thus increasing foreign gene expression. The advantage of infiltrating intact plants is the possibility to scale up foreign protein production by transient expression to levels that are commercially viable.

The present invention also teaches the targeting of HPV L1 protein to specific plant cell sub-compartments (ER and chloroplasts) by agroinfiltration or in transgenic plants. Chloroplast-targeting significantly increased L1 accumulation over ER-targeted and cytoplasmic accumulation. Chloroplast accumulation may protect L1 protein from degradation by proteases present in the cytoplasm and/or allow it to accumulate to higher concentration without affecting the function of the plant cell. The same considerations apply to the other polypeptides as hereinbefore described.

EXAMPLES

The invention will now be described with reference to the following non-limiting examples.

Example 1

Expression of HPV L1 Protein to High Levels

Expression Constructs

Three *Agrobacterium* vectors: pTRAc, pTRAkc-rbcs1-cTP and pTRAkc-ERH (FIG. 1) were obtained from Rainer Fischer (Fraunhofer Institute, Aachen, Germany). The pTRAc vector consists of a Cauliflower Mosaic Virus (CaMV) 35S promoter (P35SS), with duplicated transcriptional enhancer, chalcone synthase 5' untranslated region (CHS) and CaMV 35S polyadenylation signal (pA35S), for foreign gene expression; 2 scaffold attachment regions (SAR) for the tobacco RB7 gene; the left and right borders for T-DNA integration; origins of replication for *E. coli* and *Agrobacterium tumefaciens*; and the bla gene for antibiotic selection. pTRAkc-rbcs1-cTP is a derivative of pTRAc with an additional rbcs-cTP sequence (chloroplast targeting signal from the small subunit of Rubisco from *Solanum*), forming a 3' fusion with the foreign gene. pTRAkc-ERH is also derivative of pTRAc, and includes the KDEL and his6 sequences, forming a 5' fusion with the foreign gene. The pTRAkc-rbcs1-cTP and pTRAkc-ERH vectors also include the npt II gene, for kanamycin resistance in plants.

Four HPV-16 L1 gene variants were cloned into the above mentioned *Agrobacterium* vectors: (1) a South African isolate, SAL1 (GenBank accession no. AY177679); (2) human-codon optimised L1 (HL1, FIG. 2); (3) plant-codon optimised L1 (SYNL1, FIGS. 3), and (4) nuclear localisation signal deficient, 22 amino acid truncation of HL1, HL1AC22.

To facilitate directional cloning, restriction enzyme sites were added to the termini of the L1 genes by PCR amplification. SAL1 was amplified with sense primer: 5'-GGACGCGTTAGGT ACATGTCTCTTTGGCTGCCT (SEQ. ID NO. 1), and antisense primer: 5'-TCTAGACTCGAGTTACAGCTT ACGTTTTTTGCGTTT (SEQ. ID NO. 2), digested with Afl III and Xho I and cloned into the same sites of pTRAc, forming pTRA-SAL1; or digested with Mlu I and Xho I and cloned into the same sites in pTRAkc-rbcs1-cTP, forming pTRACTP-SAL1. SAL1 was also amplified with the above sense primer and antisense primer: 5'-AGCGGCCGC CAGCTTACGTTTTTTGCG (SEQ. ID NO. 3), digested with Afl III and Not I and cloned into the Nco I and Not I sites of pTRAkc-ERH, forming pTRAERH-SAL1.

SYNL1 was amplified with sense primer: 5'-GGACGCGTGAGATTCATGAGCCTTTGGCTC CCT (SEQ. ID NO. 4), and antisense primer: 5'-ATCTAGACTCGAGTTAGAGCTTCCTCTTCTTCCTCTT (SEQ. ID NO. 5), digested with Bsp HI and Xho I and cloned into the Afl III and Xho I sites of pTRAc, forming pTRA-SYNL1; or digested with M/u I and Xho I and cloned into the same sites in pTRAkc-rbcs1-cTP, forming pTRACTP-SYNL1. SYNL1 was also amplified with the above sense primer and antisense primer: 5'-AGCGGCCGCGAGCTTCCTCTTCTTCCTCTT (SEQ. ID NO. 6), digested with Bsp HI and Not I and cloned into the Nco I and Not I sites of pTRAkc-ERH, forming pTRAERH-SYNL1.

HL1 was amplified with sense primer: 5'-GGACGCGTGAGGTTCATGAGCCTGTGGCTGCC C (SEQ. ID NO. 7), and antisense primer: 5'-ATCTAGACTCGAGTCACAGCTTGCGCTTCTTCCG (SEQ. ID NO. 8), digested with Bsp HI and Xho I and cloned into the Afl III and Xho I sites of pTRAc, forming pTRA-HL1; or digested with MN I and Xho I and cloned into the same sites in pTRAkc-rbcs1-cTP, forming pTRACTP-HL1. HL1 was also amplified with the above sense primer and antisense primer: 5'-AGCGGCCGCCAGCTTGCGCTTCTTCCGC (SEQ. ID NO. 9), digested with Bsp HI and Not I and cloned into the Nco I and Not I sites of pTRAkc-ERH, forming pTRAERH-HL1. HL1AC22 was formed by PCR amplification of HL1, with the above sense primer, and the antisense primer: 5' TCTAGACTCGAGTCAGCCCAGGGTGAACTTAGG (SEQ. ID NO. 10), to facilitate termination before the NLS (Zhou et al. 1991). The PCR product was digested with M/u I and Xho I and cloned into the same sites in pTRAkc-rbcs1-cTP, forming pTRACTP-HL1ΔC22.

The 30B-GFPC3 mutant (GeneBank accession no. U62637) gfp gene was amplified from pBSG1057 (Biosource Technologies Inc, Vacaville, USA) with sense primer: 5' GGACGCGTT AGGTCCATGGCTAGCAAAGGAGAAG (SEQ. ID NO. 11), and antisense primer: 5' ATCTAGATTATTTGTA GAGCTCATCCATG (SEQ. ID NO. 12), digested with Nco I and Xba I and cloned into the same sites of pTRAc, forming pTRA-GFP.

Transformation of Agrobacterium

*Agrobacterium* GV3101::pMP90RK (obtained from Rainer Fischer, Fraunhofer Institute, Aachen) was made electrocompetent as described by (Shen and Forde, 1989). 50-200 ng of the above described HPV-16 L1/Agrobacterium vectors were mixed with 100 μl of electrocompetent cells in a 0.1 cm electrogap cuvette (BioRad). The cells were transformed in a GenePulser (BioRad) set at 1.8 kV, 25 μF and 200Ω.

Electroporated cells were incubated in 1 ml LB for 2 hours prior to plating on LB containing 50 $\mu g \cdot ml^{-1}$ carbenicillin, 50 $\mu g \cdot ml^{-1}$ rifampicin and 30. $ml^{-1}$ kanamycin. Positive clones were verified by isolation of plasmid DNA from recombinant *Agrobacterium* colonies, and re-transformation of plasmid DNA in *E. coli* DH5α cells and selection on 100 μg/ml ampicillin.

TABLE A

Summary of *Agrobacterium* recombinants used

| Clone | Vector | Insert | Cell compartment targeted | *Agrobacterium* strain |
|---|---|---|---|---|
| pTRA-SAL1 | pTRAc | SAL1 (South African HPV-16 L1 isolate) | cytoplasm | GV3101 |
| pTRA-SYNL1 | pTRAc | SYNL1 (plant-codon optimised HPV-16 L1) | cytoplasm | GV3101 |
| pTRA-HL1 | pTRAc | HL1 (human-codon optimised HPV-16 L1) | cytoplasm | GV3101 |
| pTRA-GFP | pTRAc | Gfp | cytoplasm | GV3101 |
| pTRACTP-SAL1 | pTRAkc-rbcs1-cTP | SAL1 | plastids | GV3101 |
| pTRACTP-SYNL1 | pTRAkc-rbcs1-cTP | SYNL1 | plastids | GV3101 |
| pTRACTP-HL1 | pTRAkc-rbcs1-cTP | HL1 | plastids | GV3101 |
| pTRACTP-HL1ΔC22 | pTRAkc-rbcs1-cTP | HL1ΔC22 (nuclear localisation signal truncation) | plastids | GV3101 |
| pTRACTP-GFP | pTRAkc-rbcs1-cTP | Gfp | plastids | GV3101 |
| pTRAERH-SAL1 | pTRAkc-ERH | SAL1 | ER | GV3101 |
| pTRAERH-SYNL1 | pTRAkc-ERH | SYNL1 | ER | GV3101 |
| pTRAERH-HL1 | pTRAkc-ERH | HL1 | ER | GV3101 |
| pTRAERH-GFP | pTRAkc-ERH | Gfp | ER | GV3101 |
| pBIN-NSs | pBIN | NSs | cytoplasm | LBA4404 |

Preparation of *Agrobacterium* for Infiltration

*Agrobacterium* LBA4404 (pBIN-NSs), containing the NSs silencing suppressors gene of TSWV, was obtained from by Marcel Prins (Laboratory of Virology, Wageningen, The Netherlands). *Agrobacterium* GV3101 cultures containing plasmids based on the pTRAc, pTRAkc-rbcs1-cTP and pTRAkc-ERH vectors were supplemented with 50 $\mu g \cdot ml^{-1}$ carbenicillin and 50 $\mu g \cdot ml^{-1}$ rifampicin. *Agrobacterium* LBA4404 (pBIN-NSs) cultures were supplemented with 50 $\mu g \cdot ml^{-1}$ rifampicin and 30 $\mu g \cdot ml^{-1}$ kanamycin. *Agrobacterium* cultures were grown shaking at 27° C. to log phase ($OD_{600} \approx 0.8$) in LB broth, containing the appropriate antibiotics. The cells were collected by centrifugation at 4000 g, resuspended in induction medium (LB broth at pH 5.6 containing 10 mM 2-[N-morpholino]ethanesulfonic acid [MES], 20 μM acetosyringone, and 2 mM $MgSO_4$) with the appropriate antibiotics, and grown as above. The cells were collected by centrifugation, as above, and resuspended in infiltration medium (10 mM $MgCl_2$, 10 mM MES, 2% sucrose and 150 $\mu g \cdot ml^{-1}$ acetosyringone, pH 5.6). For vacuum infiltration $MgCl_2$ was replaced with 4 g MS $salts \cdot l^{-1}$. The *Agrobacterium* suspensions were diluted in infiltration medium to $OD_{600}$ 1.0, and were kept at 22° C. for 2-3 h.

Agroinfiltration

Injection: The *Agrobacterium*-L1 and *Agrobacterium* (pBIN-NSs) suspensions were diluted and combined in infiltration medium, both to a final $OD_{600}$ of 0.25. When *Agrobacterium* (pTRA-GFP) was co-infiltrated with the above suspension, it was used at a final $OD_{600}$ of 0.0125. Leaves from 2-4-week-old *N. benthamiana* plants were infiltrated by injecting the *Agrobacterium* suspension into the abaxial air spaces from the underside of the leaf. Six leaves were agroinfiltrated with each agrobacterial mixture (3 plants, 2 leaves/plant). The plants were grown for 3-6 days under conditions of 16 h light, 8 h dark, 22° C.

Vacuum: *Agrobacterium* (pTRA-HL1) and *Agrobacterium* (pBIN-NSs) were grown overnight in induction medium. The cells from each culture were combined and resuspended in 1-8 litres of infiltration medium, to a final $OD_{600}$ of 0.25 per culture. Whole *N. benthamiana* plants or whole (with roots removed) *N. tabacum* L. cv. Petite Havana SR1 plants were submerged into the *Agrobacterium* suspension and subjected to a vacuum of −90 kPa for 10 min, with occasional agitation to release trapped air bubbles. The vacuum was released rapidly (−10 $kPa \cdot second^{-1}$). *N. benthamiana* plants were replanted in soil. *N. tabacum* plants stalks were placed in water-saturated floral foam. The plants were grown for 3 days under conditions of 16 h light, 8 h dark, 22° C.

Protein Extraction and Detection

Leaf disks (cap of an Eppendorf tube) were harvested from agroinfiltrated leaves, and ground in 250 μl high salt (0.5M NaCl) PBS/leaf disk. The extract was centrifuged at 13 000 rpm for 5 min in a desktop centrifuge, supernatant collected, and the centrifugation repeated. Large scale extractions were performed on vacuum-infiltrated *N. tabacum* plants: plants were homogenised with a Waring blender in 2 ml extraction buffer (0.25M sodium phosphate, 0.1M sodium metabisulphite, 10 mM EDTA, 4% polyvinylpolypyrrolidone [PVPP], pH 7.4)/g plant material. The extract was filtered through 2 layers of cheesecloth, after which the filtrate was centrifuged at 10 000 g for 20 min. The resultant supernatant was ultracentrifuged at 30 000 rpm for 3 h, and the resultant pellets were resuspended in PBS, and freeze-dried to reduce volume. Total soluble protein (TSP) concentration was determined with a Bradford assay (Sigma).

For western blot analysis, plant extracts were incubated at 85° C. for 2 min in loading buffer (Sambrook et al., 1989), separated on a 10% SDS-PAGE gel, and then transferred onto nitrocellulose membrane by semi-dry electroblotting. L1 protein was detected with H16:J4 monoclonal antibody (1:3000), and then with a goat anti-mouse alkaline phosphatase conjugate (1:10000; Sigma). Detection was performed with NBT/BCIP Tablets (Roche).

L1 protein was quantified from plant extracts by capture ELISA, modified from the polyvinyl alcohol (PVA)-blocking ELISA method of Studentsov et al. (2002). A 96-well microtitre plate was coated with monoclonal antibodies H16.J4 (binds linear HPV-16 L1 epitope) or H16.V5 (binds conformational epitope) for 1 h at 37° C., washed and blocked. Plant extract was then added for 1 h at 37° C., followed by a washing step and addition of rabbit anti-HPV-16 VLP polyclonal serum (1:1000) for 1 h at 37° C. This serum was detected with swine anti-rabbit-HRP conjugate (1:5000; DAKO, Denmark) and 1,2-phenylenediamine dihydrochloride (OPD; DAKO) substrate.

GFP was detected by Capture ELISA. Plant extracts were diluted in 1% milk solution (Elite® milk powder in PBS with 0.05% Tween 20 [PBS-T]), and incubated on a Reacti-Bind Anti-GFP coated plate (Pierce) for 1 h at 37° C. The plate was washed 4 times with PBS-T, followed by the addition of goat anti-GFP HRP conjugate (1:2000 in 1% milk solution; Abcam) the plate was incubated for 30 min at 37° C., and then washed 4 times with PBS-T. TMB substrate (KPL) was utilised for detection.

Electron Microscopy

Plant extract was immunotrapped with H16.V5 antibody (1:50) on carbon coated copper grids. The grids were stained with 2% uranyl acetate and viewed using a JEOL 200CX transmission electron microscope.

Immunisation of Mice with Plant Extract and Serum Analysis

Approximately 350 g of *N. tabacum* that had been vacuum infiltrated with *Agrobacterium* (pTRA-HL1) and *Agrobacterium* (pBIN-NSs) were extracted as described above and resuspended in 0.5 μl PBS. BALB/c mice were immunised subcutaneously with 100 μl of the plant extract (11 μg L1), either with the addition of Freund's Incomplete adjuvant (4 mice) or without (5 mice). Control groups were immunised twice with 10 μg of baculovirus-produced VLPs, or once with 1 μl of baculovirus-produced VLPs. Serum was collected from the eye vein 4 weeks post immunisation.

A modified PVA-blocking ELISA (Studentsov et al., 2002) was utilised to detect antibodies to L1 in the mice. A microtitre plate was coated with baculovirus-produced HPV-16 L1 VLPs (2 $\mu g \cdot ml^{-1}$), blocked for 2 h at 4° C. with 0.5% PVA in PBS, and then washed 6 times with PBS. Sera were serially diluted in 0.5% PVA (1:40 to 1:40960) and were incubated on the plate at 37° C. for 1 hr. After washing 6 times with PBS, rabbit anti-mouse HRP conjugate (1:2000; DAKO) was added for 30 min at 37° C. Detection was performed with OPD substrate (DAKO).

The HPV-16 pseudovirus neutralising antibody assay was performed according to the method of (Pastrana et al., 2004). The plasmids required for the assay were obtained from John Schiller (Laboratory of Cellular Oncology, National Cancer Institute, Bethesda, USA).

Plant Transformation and Regeneration

*N. tabacum* L. cv. Petite Havana SR1 leaves were cut into ±1 $cm^2$ pieces, sterilized in 10% bleach and rinsed in sterile water. Leaf discs were dipped into the relevant recombinant *Agrobacterium* culture and grown on co-cultivation media (Table 2) under constant light for two days. The leaf disks were then placed on fresh regeneration media (Table 2) every two weeks until small shoots appeared (4-6 weeks). Shoots of 1.5-2 cm were transferred to rooting media (Table 2). Shoots were incubated until strong root growth was evident, and then transplanted to a soil/vermiculite mixture (2:1), covered with plastic bags and kept away from direct light for three days before being moved to direct light. The transgenic plants were screened by PCR using the Extract-N-Amp Plant PCR kit (Sigma) and L1-specific primers.

TABLE B

Media for the transformation and regeneration of tobacco.

| | Co-cultivation | Regeneration | Rooting |
|---|---|---|---|
| α-naphtaleneacetic acid | 0.1 $mg \cdot l^{-1}$ | 0.1 $mg \cdot l^{-1}$ | |
| Benzylaminopurine | 1 $mg \cdot l^{-1}$ | 1 $mg \cdot l^{-1}$ | |
| Cefotaxime | | 250 $mg \cdot l^{-1}$ | 250 $mg \cdot l^{-1}$ |
| Kanamycin | | 300 $mg \cdot l^{-1}$ | 100 $mg \cdot l^{-1}$ |

All media contained MS with vitamins (Highveld Biological, South Africa), 1% sucrose and 0.8% agar.

The injection method of infiltration proved useful for rapid comparison of numerous *Agrobacterium* constructs, and for the optimisation of infiltration culture concentrations. Western blot analysis of *N. benthamiana* leaf samples (FIG. 4), after infiltration with *Agrobacterium* carrying the human-codon optimised HPV-16 L1 gene (HL1), demonstrated the successful expression of the 55 kDa L1 monomer. HL1 expression from the pTRA-HL1 vector (cytoplasmic localisation of L1) was not detectable after 6 days, unless co-infiltration of *Agrobacterium* (pBIN-NSs) occurred. On the other hand, chloroplast-targeted HL1 (pTRACTP-HL1 vector) produced detectable levels of HL1 without *Agrobacterium* (pBIN-NSs), which were boosted with *Agrobacterium* (pBIN-NSs) co-infiltration.

The above results were confirmed by capture ELISA (FIG. 5). Also, the ELISA established that L1 was assembling into the multimeric structures necessary for the generation of neutralising antibodies, as the H16.V5 mAb utilised for this capture ELISA is specific for a conformational epitope formed by pentamers and VLPs. The formation of VLPs were confirmed by electron microscopy (FIG. 6) of a crude extract of a *N. benthamiana* leaf that had been infiltrated with *Agrobacterium* GV3101 (pTRACTP-HL1).

Codon optimisation and plant compartment targeting affected L1 accumulation significantly (FIG. 7). The levels of SYNL1 and SAL1 accumulation in agroinfiltrated leaves were often low, or undetectable, however, HL1 accumulated to high levels (up to ~600 mg of L1/kg leaf material; ~17% of TSP). It was surprising that plant-codon optimised L1 (SYNL1) was expressed at lower levels than native L1 (SAL1). Targeting of L1 to the chloroplasts increased its accumulation significantly over both cytoplasmic and ER-targeted L1, and may be a result of protection from proteases present in the cytoplasm. L1 expression was lowest when it was targeted to the ER. *Agrobacterium* (pTRA-GFP) was utilised to measure infiltration efficiency deviations between leaves (which were generally found to be small, with a 14% difference between the most and least efficient infiltrations).

We demonstrated the potential for medium or possibly large-scale expression of HPV-L1 in *N. benthamiana* and *N. tabacum* L. cv. Petite Havana SR1 by vacuum infiltration. Vacuum infiltration of whole *N. benthamiana* plants readily occurred over 90-100% of leaf area, and over 70-90% of *N. tabacum* leaf area. By vacuum infiltration of whole plants, instead of loose leaves as described by Kapila et al. (1997), it was relatively easy to scale up infiltration to 2 kg of *N. tabacum* plant material.

A single immunisation of BALB/c mice with a crude *N. tabacum*/HL1 extract induced high HPV-16 VLP-specific antibody titres (40 960) (FIG. 8), which were equivalent to that elicited in mice after 2 immunisations with 104 of baculovirus-produced VLPs. The addition of Freund's Incomplete adjuvant to the plant extract did appear not increase the humoral response elicited to HL1, suggesting that accompanying plant proteins in the sample without Freund's Incomplete adjuvant may have adjuvant properties. An in vitro HPV-16 pseudovirus neutralisation assay was performed using the above mouse sera (Table 3). This assay is based on the ability of neutralising serum to block the entry of SEAP HPV-16 pseudoviruses into cells, thus stopping the transfer the SEAP reporter gene into the cells. Mice that had been immunised with the crude *N. tabacum*/HL1extract, successfully elicited neutralising antibody levels greater to those elicited by 2 immunisations with 10 μg of baculovirus-produced VLPs. It was surprising that the neutralising antibody levels elicited to the *N. tabacum*/HL1extract were lower when Freund's Incomplete adjuvant was added to it.

*N. tabacum* L. cv. Petite Havana SR1 plants were successfully transformed with *Agrobacterium* carrying the human-codon optimised HPV-16 L1 gene. As was observed with transient expression, chloroplast-targeted L1 accumulated to high levels in the transgenic plants (up to 60 mg of L1/kg plant material, 10.6% of the TSP) (FIG. 9). The observation that L1 was detected with the conformation-specific H16.V5 mAb from the transgenic leaf extracts suggests that capsomeres and possibly VLP formation is occurring in these plants.

TABLE C

SEAP HPV-16 pseudovirus neutralisation assay testing the induction of neutralising antibodies in mice, after immunisation with crude plant/HL1 extract.

| Antigen | Neutralisation (reciprocal of the highest serum dilution to cause at least a 50% reduction in SEAP activity) |
|---|---|
| PBS | <25 |
| Plant/Agro pTRA-HL1 | 6400 |
| Plant/Agro pTRA-HL1 + Freund's Inc. ad. | 1600 |
| Baculovirus-produced HPV-16 VLP 1 μg | <25 |
| Baculovirus-produced HPV-16 VLP 2 × 10 μg | 1600 |

Three days after *N. tabacum* L. cv. Petite Havana SR1 plants were vacuum infiltrated with *Agrobacterium* (pTRA-HL1) and *Agrobacterium* (pBIN-NSs), concentrated plant extracts were produced and used to immunised mice. Sera were taken 4 weeks post-immunisation. Neutralisation titres were defined as the reciprocal of the highest serum dilution that caused at least a 50% reduction in SEAP activity. Titres below 25 were considered negative.

Example 2

H5 HA Protein of Influenza Virus Expressed to High Levels

Plasmid Construction

The full-length gene HA gene (H5, 1704 bp, FIG. 10) of the Influenza A/Viet Nam/1194/2004 (H5N1) virus (GenBank accession no. AY651333) and a 23 amino acid-truncated HA gene (H5tr, 1635 bp, FIG. 11) were human codon optimised, and synthesised by Geneart (Germany). H5tr was truncated from nucleotide 1597-1665 to remove its membrane anchoring domain (FIG. 12): this should prevent the HA protein from being associated with cell membranes, and should allow the H5tr protein to be secreted from plant cells after appropriate processing in the ER, which may greatly assist its purification. Enzyme recognition sequences were added during the gene synthesis to facilitate cloning.

The H5 and H5tr genes were each cloned into the three *A. tumefaciens* vectors, in Example 1. The H5 and H5tr genes were digested with Nco I and Xba I and cloned into the Afl III and Xba I sites of pTRAc, forming the clones pTRA-H5 and pTRA-H5tr. For cloning into pTRAkc-ERH, both vector and H5/H5tr genes were digested with Nco I and Not I, forming pTRAERH-H5 and pTRAERH-H5tr. The H5 and H5tr genes were digested with Mlu I and Xba I and cloned into pTrakc-rbcs1-cTP, forming the clones pTRACTP-H5 and pTRACTP-H5tr. A fourth set of clones, pTRAa-H5 and pTRAa-H5tr, was constructed by cloning the H5 and H5tr genes (digested with Nco I and Xba I) into the pTRAkc-ERH vector after Nco I and Xba I digestion, thus removing the ER retention signal (SEKDEL) to create apoplastic-targeting constructs.

*Agrobacterium* Transformation

*Agrobacterium* transformation was performed as in example 1.

Agroinfiltration

Recombinant *A. tumefaciens* GV3101 cultures containing the H5 and H5tr binary vector clones, and *A. tumefaciens* GV3101 (pTRA-P19), containing the p/9 silencing suppressor gene of tomato bushy stunt virus, were grown shaking at 27° C. to log phase ($OD_{600}$≈0.8) in LB broth supplemented with 50 μg·ml$^1$ carbenicillin, 50 μg·ml rifampicin and 30 μg·ml$^1$ kanamycin. The cells were collected by centrifugation at 4000 g, resuspended in induction medium (LB broth at pH 5.6 containing 10 mM MES, 20 μM acetosyringone, and 2 mM $MgSO_4$) with the appropriate antibiotics, and grown as above. The cells were collected by centrifugation, as above, and resuspended in infiltration medium (10 mM $MgCl_2$, 10 mM MES, 2% sucrose and 150 μg·ml$^{-1}$ acetosyringone, pH 5.6). The *A. tumefaciens* suspensions were diluted in infiltration medium to $OD_{600}$ 1.0, and were kept at 22° C. for 2-3 h.

*A. tumefaciens*-H5 or *A. tumefaciens*-H5tr suspensions were combined with *A. tumefaciens* (pTRA-P19) and diluted with infiltration medium to a final $OD_{600}$ of 0.25 for each culture. Leaves from *N. benthamiana* plants were infiltrated by injecting the bacterial suspension into the abaxial air spaces from the underside of the leaf. Four leaves were agroinfiltrated with each agrobacterial mixture. The plants were grown for 6 days under conditions of 16 h light, 8 h dark, 22° C.

Protein Extraction and HA Detection

*N. benthamiana* leaf disks (cut using the cap of a 2 ml microfuge tube) were harvested from agroinfiltrated leaves, and ground in 250 μl high salt phosphate buffer (0.5 M NaCl)/disk. The extract was centrifuged at 13 000 rpm for 5 min, supernatant collected, and the centrifugation repeated.

The samples were tested for presence of HA by western blot analysis. Plant extracts were incubated at 85° C. for 2 min in loading buffer {Sambrook, 1989 33369/id}, separated on a 10% SDS-PAGE gel, and then transferred onto nitrocellulose membrane by semi-dry electroblotting. HA protein was detected with H5 positive chicken serum (1:000; James Kitching, Elsenburg, Western Cape Dept of Agriculture), rabbit anti-chicken serum (1:1000; Ed Rybicki, UCT), and then with swine anti-rabbit alkaline phosphatase conjugate (1:10 000; Sigma). Detection was performed with NBT/BCIP Tablets (Roche).

Agroinfiltration proved useful to rapidly compare the expression of numerous HA constructs in plants. Preliminary results show that the highest accumulation of HA protein was obtained when using the pTRAERH-H5 and pTRAERH-H5tr constructs, which target protein to the ER (FIG. 13). HA could not be detected the when using the other constructs.

Example 3

Plasmid Construction

*Agrobacterium* vectors pTRAc, pTRAkc-ERH,pTRAkc-A, and pTRAkc-rbcs1-cTP (FIG. 14) were supplied by Rainer Fischer (Fraunhofer Institute for Molecular Biology and Applied Ecology IME, Aachen, Germany). Restriction enzyme sites were included at either end of the L2 ORF by polymerase chain reaction (PCR), to facilitate directional cloning into the three *Agrobacterium* vectors. The wild type HPV-16 L2 1.4 kb open reading frame (ORF) (saL2), the HPV-16 L2 ORF codon optimized for expression in plants (plantised) and the codon optimized HPV-16 L2 ORF for mammalian expression (humanised) were amplified by PCR. Codon optimization for *Nicotiana* of HPV-16 L2 (pL2) was done by GENEART® (Regensberg, Germany). The humanised HPV-16 L2 (hL2) was supplied by Martin Müller (Germany).

The pTRA vectors hold a number of characteristics that optimize the expression of the foreign gene. pTRAc contains the skeleton features and is proficient at transgene expression in the cytoplasm of plant cells (FIG. 14). The pTRAkc-ERH vector includes all the characteristics of pTRAc with a few additions (FIG. 14). A kanamycin resistance gene (nptII) was added, this allows these vectors to be used for the generation of transgenic plants. In this study however, transient expression was utilised. pTRAkc-ERH also includes sequences resulting in the carboxy terminal fusions of a His tag and endoplasmic reticulum (ER) retention signal (KDEL). The KDEL sequence is thought to retard proteins at the ER, where they may be protected from degradation. The KDEL sequence may infer protection against degradation as proteins that are unable to form their final conformation remain in the ER (1). Proteins present in the ER that do not have a KDEL sequence are degraded (1). The pTRAkc-A vector is derived from the pTRAkc-ERH vector, it contains the secretory signal 'LPH' but lacks the 'KDEL', thus the protein is secreted out of the cell into the apoplastic space. The pTRAkc-rbcs1-cTP vector which is based on pTRAc, also includes the short stroma-targeting domain (STD) sequence, rbcs1-cTP, which forms an amino terminal STD fusion with the foreign protein. Proteins probably cross where the inner and outer membranes meet, once within the stroma the STD is processed by a 140 kDa metalloprotease (2).

The left and right borders flank the region of DNA that will be transferred to the plant cell, the T-DNA. The scaffold attachment regions, also known as matrix attachment regions, are on either side of the transgene. These regions are thought to interact with nuclear matrix proteins forming loop domains in DNA which has been shown to increase expression with insertion in a plasmid (3). Expression of the transgene is controlled by a dual P35S CaMV promoter, with a duplicated transcriptional enhancer. This promoter has been shown to increase expression over the traditional single P35S CaMV (4). The polyadenylation signal of the P35S gene is fused to the end of the foreign gene; this stabilizes RNA transcripts. Replication of the plasmid in *Agrobacterium* is initiated at the RK2 origin of replication. Due to the low copy number of the plasmid in *Agrobacterium*, the vector can alternatively be replicated in *Escherichia coli* using the ColE1 origin of replication (5). The development of resistance by a number of *Agrobacterium* to ampicillin has lead to the fusion of carbenicillin and ampicillin resistance in the bla gene. Ampicillin is used as a marker in *E. coli* with carbenicillin as a marker in *Agrobacterium.*

Cloning of all genes into their respective vectors was done using the applicable primer pair. The saL2 ORF was amplified with the primer pair F L2-ERH and R L2-pTRAc (Table 1). The primer pair F $_{P}$L2-pTRAc and R $_{P}$L2-pTRAc was used to amplify the pL2 ORF, and the F-hL2-pTRAc and R hL2-pTRAc pair were used to amplify the hL2 ORF to facilitate cloning into pTRAc. The 1.4 kb fragments were cloned into pGEM®-T easy (PROMEGA) and sequenced to confirm PCR fidelity. saL2 was excised with restriction enzymes BspHI and XbaI and subcloned into the AflIII and XbaI sites of pTRAc making plasmid pTRA-saL2-C. Restriction enzymes BspHI and BamHI were used to excise pL2 which was subcloned into the AflIII and BamHI sites of pTRAc making plasmid pTRA-pL2-C. hL2 was cloned using restriction enzymes BspHI and XbaI to make plasmid pTRA-hL2-C.

In order to clone saL2 into pTRAkc-ERH, the saL2 ORF was amplified with the primer pair F L2-ERH and R L2-ERH (Table 1), and cloned into the NcoI and NotI sites of pTRAkc-ERH using BspHI and NotI, making plasmid pTRA-saL2-E. Similarly the hL2 ORF was cloned into pTRAkc-ERH using the primer pair F hL2 pTRAc and R hL2-pTRA E.

TABLE 1

Primers used in PCR with their sequence and the restriction sites they attach

| Primer Name | Sequence | Underlined Restriction Site |
|---|---|---|
| F L2-ERH | GCTCATGAGACACAAACGTTCTGCAAAAG | BspHI |
| R L2-ERH | AAGCGGCCGCGGCAGCCAAAGAGACATC | NotI |
| R L2-pTRAc | AATCTAGACTAGGCAGCCAAAGAGAC | XbaI |
| F L2-Plast | AAACGCGTTAGGTGCATGAGACACAAACGTTCTGCAAAAC | MluI |
| F pL2-pTRAc | AATCATGAGACATAAGAGATCTGCTAAG | BspHI |
| R pL2-pTRAc | CGGGATCCCTAAGCAGCAAGAGAAACATC | BamHI |
| F pL2-cTP | GGACGCGTTAGGTGCATGAGACATAAGAGATCTGC | MluI |
| F hL2-pTRAc | ATTCATGAGGCACAAGAGGAGCGCC | BspHI |
| R hL2-pTRAc | ATTCTAGATCAGGCGGCCAGGCTCAC | XbaI |

TABLE 1-continued

Primers used in PCR with their sequence and the restriction sites they attach

| Primer Name | Sequence | Underlined Restriction Site |
|---|---|---|
| F hL2-pTRA-P | ATACGCGTTAGGTGCATGAGGCACAAGAGGAGC | MluI |
| R hL2-pTRA-E | ATGCGGCCGCGGCGGCCAGGCTCACGTC | NotI |

Sequences highlighted in red indicate the start codon of the 1.2 ORF.
Sequences highlighted in blue indicate the stop codon of the 1.2 ORF.

For cloning into pTRAkc-rbcs1-cTP, saL2, pL2 and hL2 were PCR amplified with the primer pairs F L2-Plast and R L2-pTRAc, F pL2-cTP and R pL2-pTRAc, and F hL2-pTRA-P and R hL2-pTRAc respectively (Table 1). hL2 and saL2 were further cloned using enzymes MluI and XbaI into the MluI and XbaI sites of pTRAkc-rbcs1-cTP, forming the plasmid pTRA-saL2-P and pTRA-hL2-P. MluI and BamHI were used to clone pL2 into the MluI and BamHI sites of pTRAkc-rbcs1-cTP, creating pTRA-pL2-P.

The pTRA-hL2-A clone was made by cloning the same BspHI and XbaI fragment used to make pTRA-hL-C and cloned into the BspHI-XbaI fragment of pTRAkc-ERH Generation of Recombinant *Agrobacterium*

*Agrobacterium tumefaciens* GV3101 was provided by Rainer Fischer (Fraunhofer Institute for Molecular Biology and Applied Ecology IME, Aachen, Germany). The GV3101 strain contains the helper plasmid, pMP90RK, which contains the crucial vir genes (5). The pTRA vectors, as mentioned previously, can be replicated in *E. coli* as well as in *Agrobacterium*. The vector constructs were first cloned into DH5α cells, which are easier to culture and have a higher copy number of the plasmid in comparison with *Agrobacterium* (5). *Agrobacterium* GV3101 cells were grown to log phase 0.8 $OD_{600}$ at 26° C. with shaking, in Luria broth (LB) containing antibiotics; 50 μg/ml rifampicin (Rif) and 30 μg/ml kanamycin (Kan). Cells were made electrocompetent by washing 3 times with Milli-Q water and resuspended in 1/20 the culture volume with 10% glycerol. Plasmid DNA concentration isolated from DH5α cells was determined by UV spectrometry at 260 nm. Plasmid DNA (400 ng) was mixed with 100 μl of electro-competent GV3101 cells in a 0.1 cm cuvette (BIORAD®), and electroporated using the following parameters 200Ω, 25 μF, and 1.5 kV (Gene Pulse, BIO-RAD®). After incubation at 26° C. in Luria broth (LB) for 1 hour the electroporated cells were plated on Luria agar (LA), containing 50 μg/ml Rif, 30 μg/ml Kan, and 50 μg/ml carbenicillin (Garb) and grown at 26° C. for 3-4 days.

Successful transformation was determined either by colony PCR, or by restriction enzyme analysis. Due the low plasmid copy number in *Agrobacterium*, the plasmid from successfully electroporated GV3101 colonies were extracted and transformed into *E. coli* to obtain sufficient DNA for restriction analysis. This was accomplished by inoculating LB containing Rif, Kan, and Carb with *Agrobacterium* colonies which had grown at 26° C. on the luria agar. Competent DH5α cells were transformed with isolated plasmid DNA from the *Agrobacterium* and plated on LA with 100 μg/ml ampicillin incubated at 37° C., O/N. Five DH5α colonies for each viable *Agrobacterium* colony were used to inoculate LB containing 100 μg/ml ampicillin grown at 37° C. to log phase. Cultures were used for small-scale plasmid DNA preparation and restriction digest analysis was undertaken to determine if the insert was present. Glycerol stocks of the suitable *Agrobacterium* colony were made. nine L2 *Agrobacterium* GV3101 strains were made containing the plasmids: pTRA-saL2-E, pTRA-saL2-C, pTRA-saL2-P, pTRA-pL2-C, pTRA-pL2-P, pTRA-hL2-A, pTRA-hL2-C, pTRA-hL2-E, and pTRA-hL2-P (Table 2).

Plant Lines

Wild type *Nicotiana benthamiana* were grown under conditions of 16 h light, 8 h dark at 22° C. Plants were utilised 14-28 days after being transplanted from seedling trays to pots.

Preparation of Agrobacterium for Infiltration

The infiltration protocol simulates the natural process of *Agrobacterium* induction by acetosyringone. The induction and infiltration medium both contain acetosyringone which activates the various vir genes (6). *Agrobacterium* strains were grown from glycerol stocks in LB with Rif, Kan, and Carb to an $OD_{600}$ between 1 and 2 at 26° C. *Agrobacterium* was centrifuged at 5,000×g for 10 min at room temperature (RT) and resuspended in induction medium (LB, 10 mM 2-[N-morpholino]ethanesulfonic acid [MES], 2 mM $MgSO_4$, 20 μM acetosyringone, pH 5.6, with Rif, Carb, and Kan) and grown to an $OD_{600}$ of between 1 and 2 at 26° C. Cells were centrifuged at 5,000×g for 10 min at RT and resuspended in infiltration medium (10 mM MES, 10 mM $MgCl_2$, 2.2105 g/l Murashige Skoog [MS] salts, 35 g/l sucrose, 150 μM acetosyringone, at pH 5.6). The optical density of the cells were measured and diluted to an $OD_{600}$ of between 0.4 and 1.0. The cells were incubated for 3 h in the infiltration medium before infiltration.

TABLE 2

A summary of *Agrobacterium* strains, the vectors that were used, the plasimds made, the inserts they contain and where the heterologous protein is targeted

| *Agrobacterium* Strain | *Agrobacterium* Vector | Plasmid Name | Insert | Cell Compartment Targeted |
|---|---|---|---|---|
| GV3101 | pTRAc | pTRA-saL2-C | HPV-16 saL2 | cytoplasm |
| GV3101 | pTRAkc-ERH | pTRA-saL2-E | HPV-16 saL2 | endoplasmic reticulum |
| GV3101 | pTRAkc-rbcs1-cTP | pTRA-saL2-P | HPV-16 saL2 | chloroplast |
| GV3101 | pTRAc | pTRA-pL2-C | HPV-16 pL2 | cytoplasm |
| GV3101 | pTRAkc-rbcs1-cTP | pTRA-pL2-P | HPV-16 pL2 | chloroplast |

TABLE 2-continued

A summary of *Agrobacterium* strains, the vectors that were used, the plasimds made, the inserts they contain and where the heterologous protein is targeted

| *Agrobacterium* Strain | *Agrobacterium* Vector | Plasmid Name | Insert | Cell Compartment Targeted |
|---|---|---|---|---|
| GV3101 | pTRAc | pTRA-hL2-C | HPV-16 hL2 | cytoplasm |
| GV3101 | pTRAkc-A | pTRA-hL2-A | HPV-16 hL2 | apoplastic space |
| GV3101 | pTRAkc-ERH | pTRA-hL2-E | HPV-16 hL2 | endoplasmic reticulum |
| GV3101 | pTRAkc-rbcs1-cTP | pTRA-hL2-P | HPV-16 hL2 | chloroplast |
| *GV3101 | pTRAc | pTRA-HL1 | HPV-16 HL1 | cytoplasm |
| *GV3101 | pTRAc | pTRA-p19 | p19 | cytoplasm |

**Agrobacterium* strains supplied by James MacLean
HPV-16 saL2 - wild type L2 ORF.
HPV-16 pL2 - L2 ORF optimized for expression in *Nicotiana*.
HPV-16 saL1 - wild type L1 ORF.
HPV-16 hL1 - L1 ORF optimized for expression in *Homo sapiens*.

Infiltration Procedure

A mammalian optimized HPV-16 L1 gene in GV3101 cloned into the cytoplasmically targeted vector (pTRA-hL1) was kindly given by Dr. James MacLean (UCT, Cape Town, South Africa) *Agrobacterium* GV3101 strains containing L2 or L1 constructs were either infiltrated alone or mixed with equal amounts of GV3101 (pTRA-p19) which codes for a silencing suppressor p19, this strain was also kindly donated by Dr. James MacLean (UCT, Cape Town, South Africa). Two different infiltration protocols were used; injection infiltration or infiltration under a vacuum. For injection infiltration a 2 ml syringe was used to inject the *Agrobacterium* suspended in infiltration medium into the abaxial air spaces of *N. benthamiana* leaves.

For vacuum infiltration whole *N. benthamiana* plants were suspended in infiltration medium containing the *Agrobacterium* strains and placed under vacuum at 60 mbar for 5 min. *Agrobacterium* was infiltrated with the release of the vacuum. The protocol differs to that used by Vaquero et al. (1999) (7). Whole plants were uprooted, vacuum infiltrated and replanted. Vaquero et al. (1999) vacuum infiltrated whole leaves of Petite Havanna plants. Use of whole plants is not only easier but additional nutrients may be given to the leaves to increase transgene expression. Plants are subsequently incubated at 28° C. in a humidity-controlled room.

Protein Extraction and Western Blots

Homogenization was done by grinding the material in liquid nitrogen. Homogenized sample was suspended in 2 μl/mg of 8M urea. Cell debris and other larger molecules were separated by two centrifugation rounds (10,000×g, 10 min at RT). Sodium dodecyl sulphate (SDS)—PAGE loading buffer was added to the samples and boiled for 10 min. Sample was loaded onto a 10% SDS-PAGE and run at 100 V for ~2.5 h. Protein was transferred to nylon membrane (Nitrobind, Cast, Pure nitrocellulose, 0.45 micron, OSMONICS INC.) by semi-dry blotting at 15 V, 400 mA, for 2 h (Trans Blot® semi-dry, BIORAD® with the power supply Electrophoresis Power Supply, AMERSHAM®). The success of transfer was measured by coomassie blue staining of the gel after transfer. The membrane was blocked 0/N in 5% skimmed milk suspended in PBS with 0.05% Tween-20. The membrane was incubated for a further 4 hours at RT with rabbit polyclonal antiserum raised against HPV-16 L2 (1:3,000), mouse monoclonal antibodies against HPV-16 L1 (J4) (1:5,000). Membranes were incubated with goat-anti-rabbit or goat-anti-mouse antibodies conjugated with alkaline phosphatase (SIGMA®-Aldrich) diluted to 1:10,000 for 2 h at RT. Immunodetection was done using 5-Bromo-4-Chloro-3-indolyl phosphate/Nitroblue tetrazolium (BCIP/NBT) made according to manufacturer instructions (ROCHE® Diagnostics).

Expression of L2 by Transient Expression in *N. benthamiana* Plants.

*N. benthamiana* plants were infiltrated with all nine *Agrobacterium* strains containing the different L2 ORFs. Expression of L2 was unable to be detected by western blot any of the strains containing the pL2 ORF or the saL2 ORF (data not shown). This could be due to codon usage as has been previously published for L1. (8) Expression was however noted when expressed from any of the clones having the hL2 gene (FIG. 15). Similar expression of L2 across the suite of vectors was noted. Similar amounts of degradation products were also noted in the different vectors. This possibly indicates that L2 is localized to the same region of the plant cell despite signalling molecules within the vector. A certain degree of protection particularly by the chloroplast-targeted proteins would be expected. These figures contradict other findings made with these vectors, for example, L1 expression is markedly less with the ER-targeted vector than that of the chloroplast- or cytoplasmic-targeted vectors. (Dr. James MacLean, personal communication)

L2 Appears to be Highly Expressed.

Plant material from each infiltration was weighed and thus the same amount of buffer (8M urea) was added. This allows the possibility of empirically determining the original weight of plant material that was loaded on a western (FIG. 3). This immunoblot shows that L2 can still be detected up to 0.4 mg of original plant material. We can only speculate the amount of L2 that is present relative to total soluble protein, further analysis by ELISA was attempted but unsuccessful due to only a polyclonal antibody being available.

Co-expression of L1 and L2 in the Same Region.

L2 and L1 were simultaneously co-infiltrated into *N. benthamiana* plants. Expression of both L1 and L2 was able to be detected in these leaf samples, however from these results it is inconclusive whether L1 and L2 are being expressed in the same cell. The literature suggests that they are more than likely being expressed in the same cell, with expression of antibodies with multiple subunits that form, having been proven. (29)

Immune responses against L1 have been shown to produce type-specific antibodies, with the advent of the GSK and Merck HPV vaccines this has paved the way for second generation vaccines that will more than likely incorporate L2 and its cross-neutralizing properties. The production of heterologous proteins and in particular subunit vaccines in plants has been shown to be more cost effective than other expression systems. In conclusion a marriage of these two simple yet important ideals could lead to what is needed most in the fight against cervical cancer: a cheap and effective vaccine.

Example 4

Chimaeric HPV L1 Protein Expressed to High Levels

The method described in WO2003/097673, which document is incorporated herein by reference, is used for high level expression of chimaeric HPV L1 proteins as hereinbefore described.

FIGURES

The specification should be read with reference to the following figures in which:

FIG. 2 shows Human-codon optimised HPV-16 L1 (HL1) (SEQ. ID NO. 13).

FIG. 3 shows Plant-codon optimised HPV-16 L1 (SYNL1) (SEQ. ID NO. 14).

Figure 1:
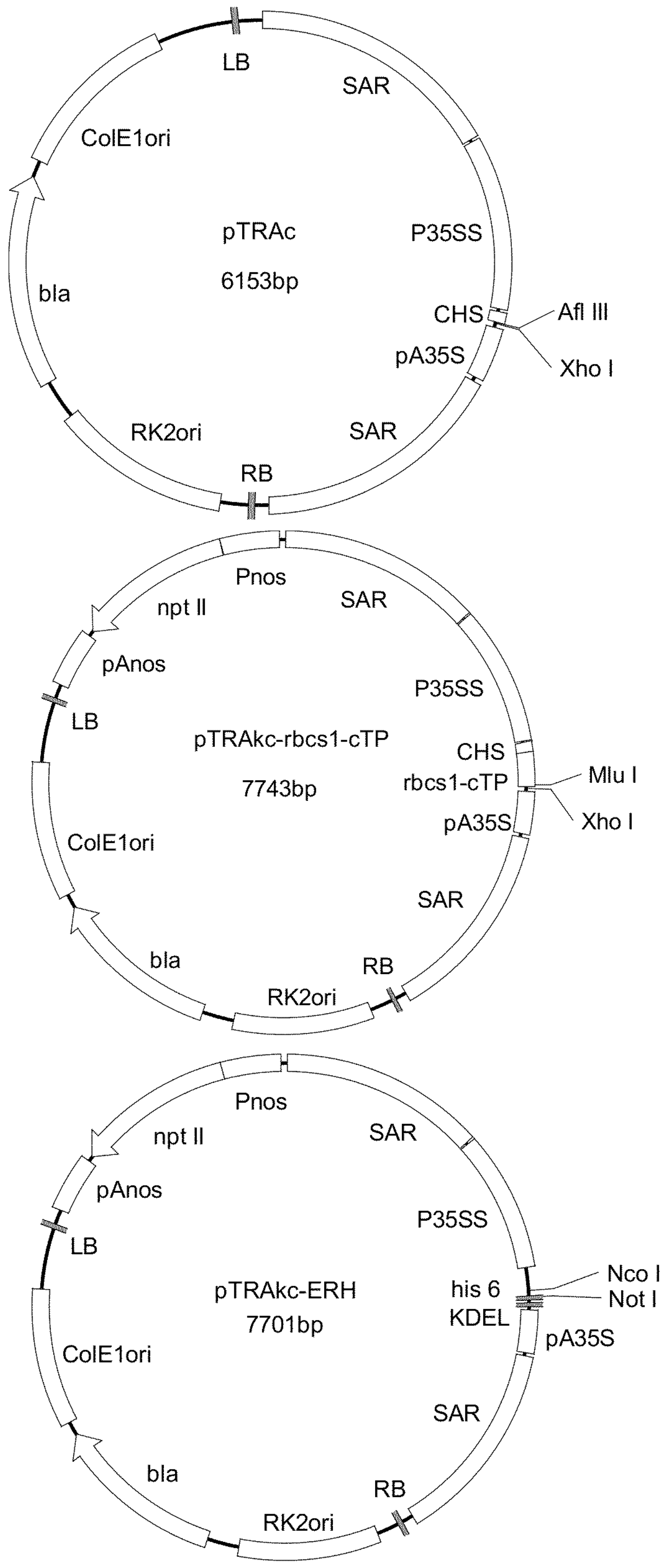
FIG. 1 shows *Agrobacterium* vectors pTRAc, pTRAkc-rbcs1-cTP and pTRAkc-ERH.
Figure 4:
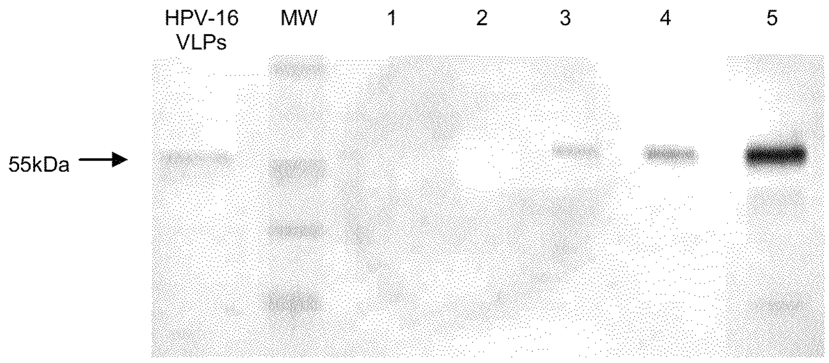

FIG. 4 shows a western blot of *N. benthamiana* leaf samples after infiltration with *Agrobacterium* carrying the HPV-16 L1 gene. *N. benthamiana* leaves were infiltrated by injection with an *Agrobacterium*-L1 construct, or co-infiltrated with *Agrobacterium*-L1 and *Agrobacterium* (pBIN-NSs). The western blot was performed on crude leaf extracts 6 days post infiltration, using H16.J4 anti-HPV-16 L1 monoclonal antibody. The samples in lanes 1-5 were from leaves infiltrated with *Agrobacterium* carrying the following vectors: 1, pTRACTP-GFP; 2, pTRA-HL1; 3, pBIN-NSs and pTRA-HL1; 4, pTRACTP-HL1; 5, pBIN-NSs and pTRACTP-HL1.

Figure 5:
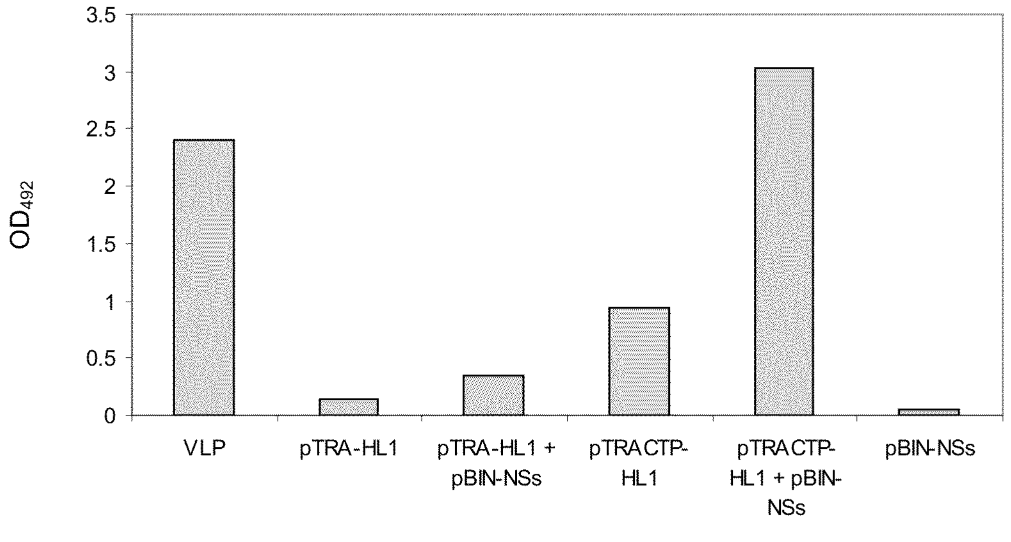

FIG. 5 shows detection of L1 in *N. benthamiana* leaf samples after infiltration with *Agrobacterium* carrying the HPV-16 L1 gene. *N. benthamiana* leaves were infiltrated by injection with an *Agrobacterium*-L1 construct, or co-infiltrated with *Agrobacterium*-L1 and *Agrobacterium* (pBIN-NSs). Six days post infiltration crude leaf extracts were assessed by a H16.V5 capture ELISA.

Figure 6:
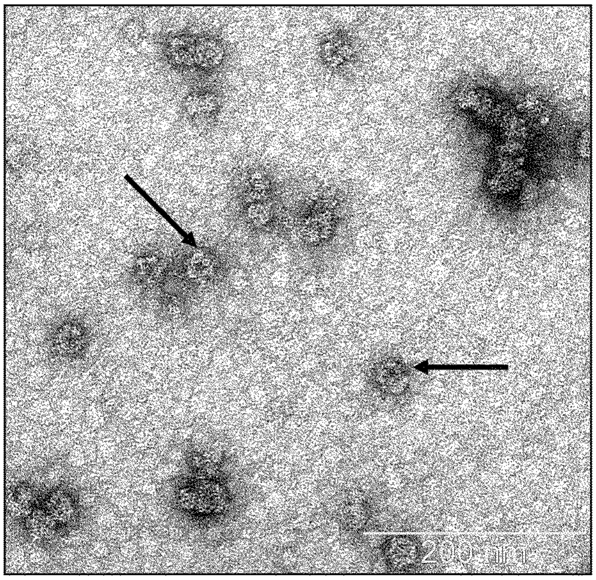

FIG. 6 shows electron micrograph of crude *N. benthamiana* plant extract after infiltration with *Agrobacterium* GV3101 (pTRACTP-HL1). VLPs are indicated by the arrows.

Figure 7:
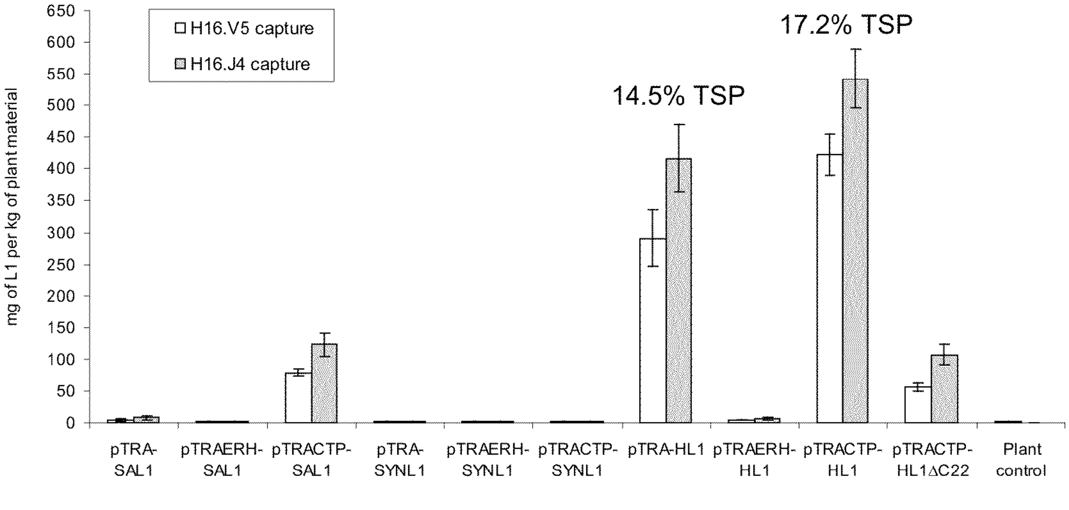

FIG. 7 shows milligrams of HPV-16 L1 produced in plants by agroinfiltration. *N. benthamiana* leaves were infiltrated a mixture of an *Agrobacterium*-L1 construct, *Agrobacterium* (pBIN-NSs), and *Agrobacterium* (pTRA-GFP). Six days post infiltration crude leaf extracts were assessed by H16.V5 and H16.J4 mAb capture ELISAs. The L1 level expressed as a % of the total soluble protein (TSP) is displayed for specific constructs.

Figure 8:
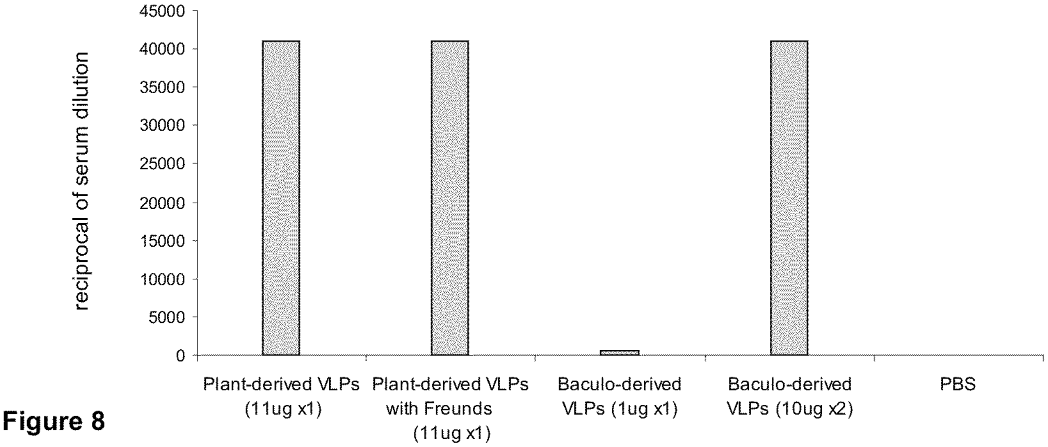

FIG. 8 shows HPV-16 VLP-specific systemic antibody titres induced in BALB/c mice after a single immunisation with a crude plant/HL1 extract. Three days after *N. tabacum* L. cv. Petite Havana SR1 plants were vacuum infiltrated with *Agrobacterium* (pTRA-HL1) and *Agrobacterium* (pBIN-NSs), concentrated plant extracts were produced, and used to immunised mice. Control groups were immunised twice with 10 μg of baculovirus-produced VLPs, or once with 1 μg of baculovirus-produced VLPs. Sera were taken 4 weeks post-immunisation, serially diluted (pooled for each group of mice) and used in an ELISA against HPV-16 VLPs. The OD 492 nm values were measured and the results recorded as the reciprocal of the highest dilution where the OD is >2x that of the prebleed.

Figure 9:
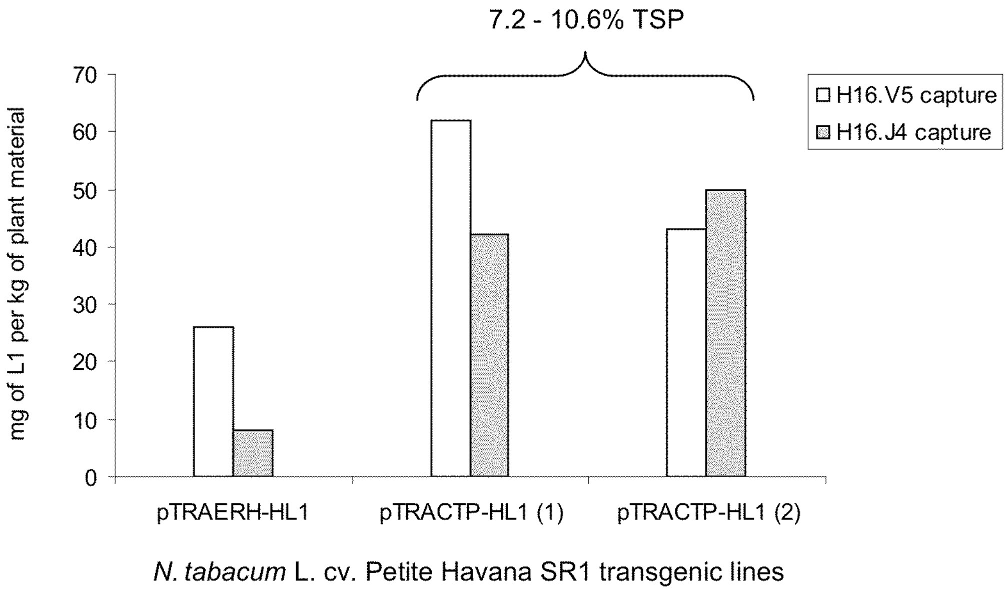

FIG. 9 shows milligrams of HPV-16 L1 produced per kg of transgenic plant material. *N. tabacum* L. cv. Petite Havana SR1 plants were transformed with *Agrobacterium* carrying the HPV-16 L1 gene. L1 was detected in crude leaf extracts by H16.V5 and H16.J4 mAb capture ELISAs. The L1 level expressed as a % of TSP is displayed for specific constructs.

FIG. 10 shows a human codon optimised full-length gene HA gene (H5, 1704 bp) of the Influenza A/Viet Nam/1194/2004 (H5N1) virus (GenBank accession no. AY651333) (SEQ. ID NO. 15).

FIG. 11 shows a 23 amino acid-truncated human codon optimised HA gene (H5tr, 1635 bp). H5tr was truncated from nucleotide 1597-1665 to remove its membrane anchoring domain (SEQ. ID NO. 16).

FIG. 12 shows the transmembrane prediction for the H5 gene (CBS Prediction Servers, http://www.cbs.dtu.dk).

Figure 13:
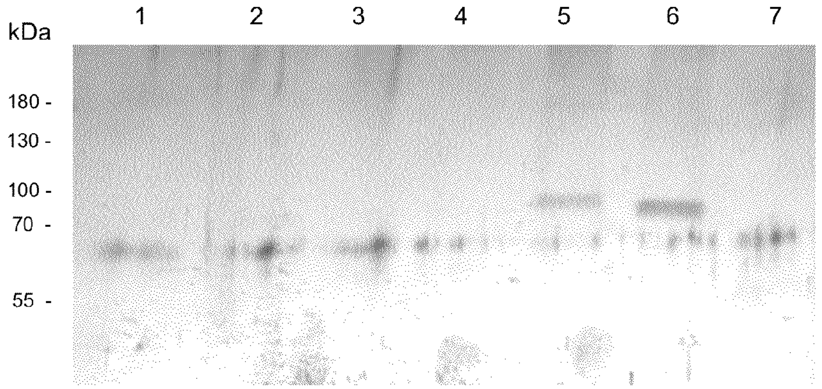

FIG. 13 shows the Western blot of *N. benthamiana* leaf samples after infiltration with *Agrobacterium* carrying the H5 or H5tr genes. The *Agrobacterium* samples were as follows: 1, pTRA-H5; 2, pTRA-H5tr; 3, pTRACTP-H5; 4, pTRACTP-H5tr; 5, pTRAERH-H5; 6, pTRAERH-H5tr. Lane 7 contained non-infiltrated *N. benthamiana* extract.

Figure 14:
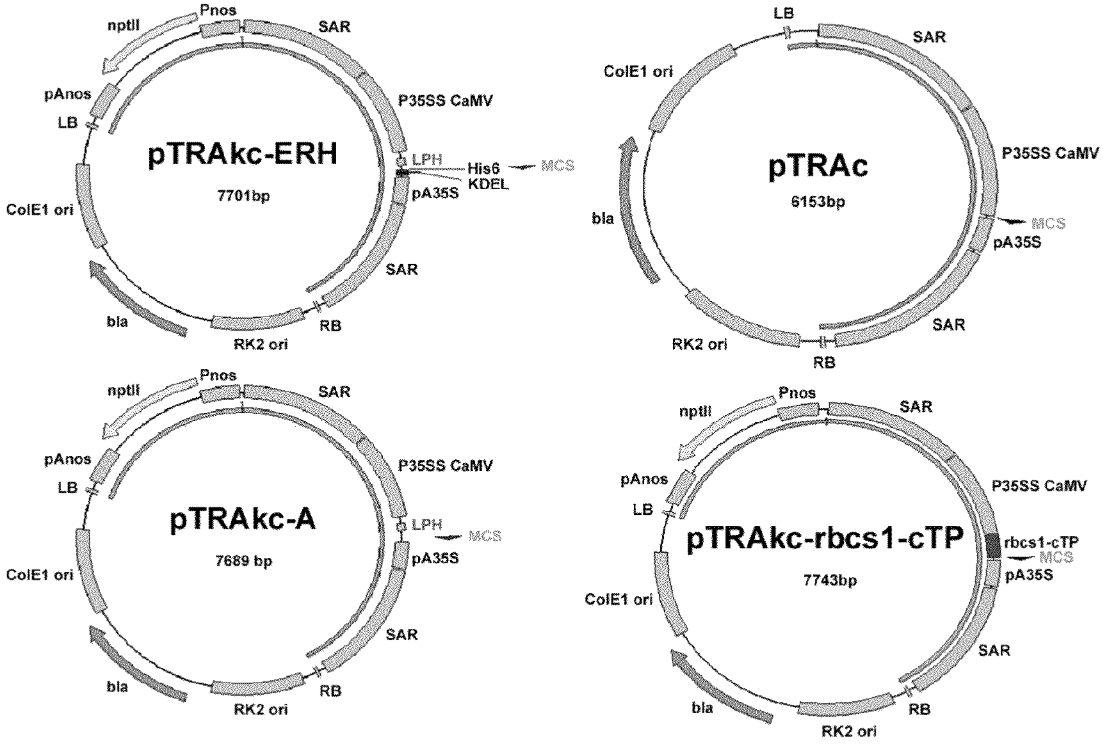

FIG. 14 shows *Agrobacterium* vectors utilised in this study, namely pTRAc, pTRAkc-ERH, pTRAkc-rbcs1-cTP, and pTRAkc-A. The light blue bar indicates the T-DNA that is transferred to the plant cell at transfection. The heterologous gene is cloned into the vectors at the multiple cloning site (MCS). The vectors share a number of common features indicated by regions in grey. The T-DNA region is flanked by the left border (LB) and the right border (RB). At either end of the MCS are scaffold attachment regions (SAR). Expression of the transgene is controlled by a dual 35S Cauliflower Mosaic Virus promoter (P35SS CaMV) with attachment of the polyadenylation signal of the same CaMV gene (pA35S). Replication of the vector in *Agrobacterium* is initiated at the RK2 ori. A separate replication initiation site, ColE1, is used in *E. coli*. The pTRAc vector contains only one antibiotic resistance marker (bla) allowing selection with ampicillin/carbenicillin. The pTRAkc-ERH, pTRAkc-A, and pTRAkc-rbcs1-cTP contain a second antibiotic marker (nptII) permitting selection with kanamycin in plants. The nptII gene is controlled by the promoter of the *Agrobacterium* gene nopaline synthase (Pnos), the polyadentlation of the same gene is attached to nptII (pAnos). pTRAkc-ERH additionally includes a secretory signal (LPH), His tag (His6) sequence and an endoplasmic reticulum retention signal (KDEL) sequence downstream of the MCS. pTRAkc-rbcs1-cTP includes a chloroplast signalling peptide (rbcs1-cTP) sequence upstream of the MCS.

Figure 15:
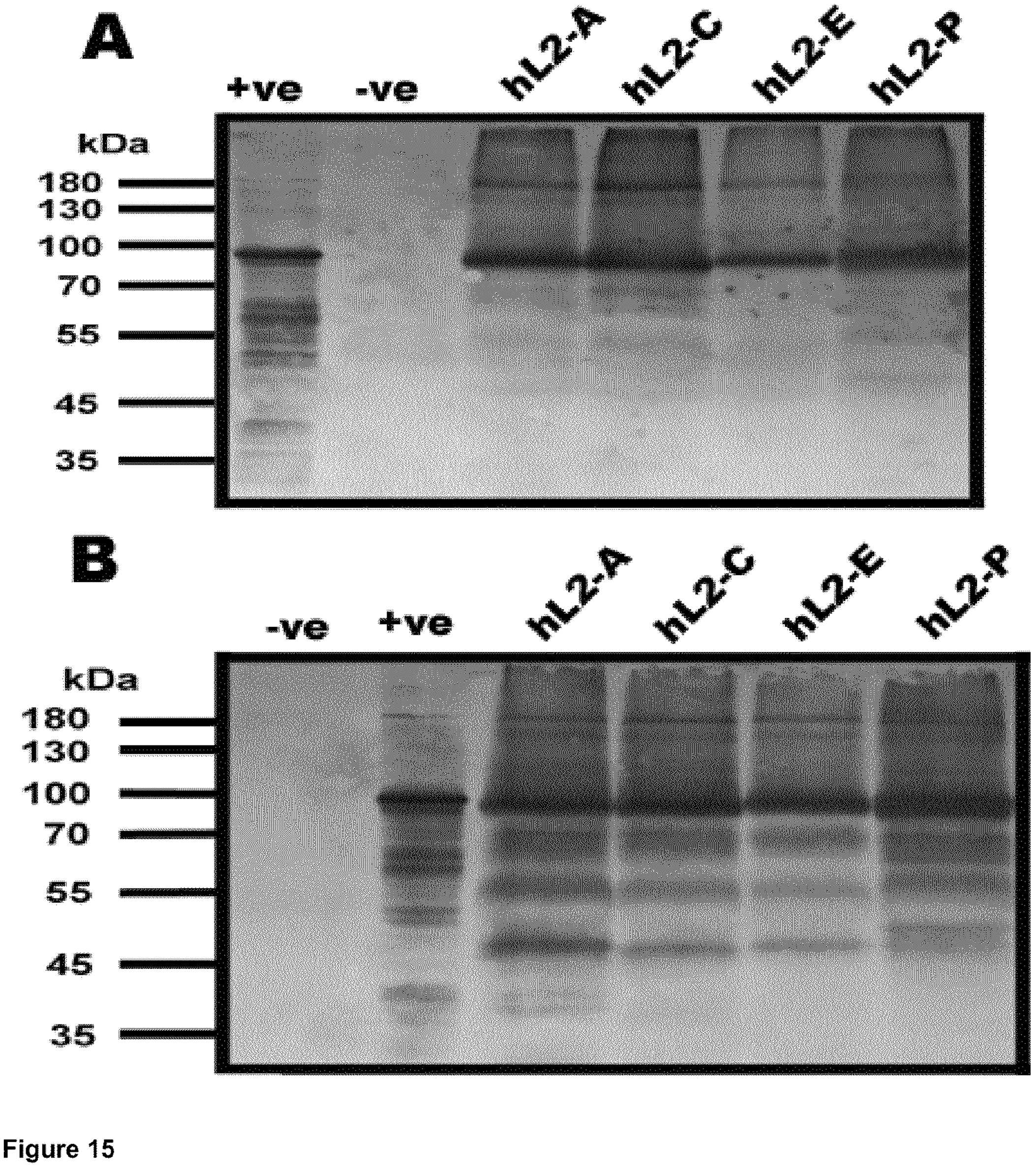

FIG. 15 shows that expression of L2 can be detected with each of the four vectors. *N. benthamiana* was transiently infiltrated with the same OD of *Agrobacterium* containing the different vectors that have the humanised L2 gene. These are pTRA-hL2-A (hL2-A), pTRA-hL2-C (hL2-C), pTRA-hL2-E (hL2-E), and pTRA-hL2-P (hL2-P). As a negative control plant material that had not been infiltrated with *Agrobacterium* were also extracted (−ve). *E. coli*-expressed HPV-16 L2 was used as a positive control (+ve) Plant material was extracted after two days (A) and five days (B) and immunoblotted. Westerns were probed using the rabbit pAb-αL2.

Figure 16:
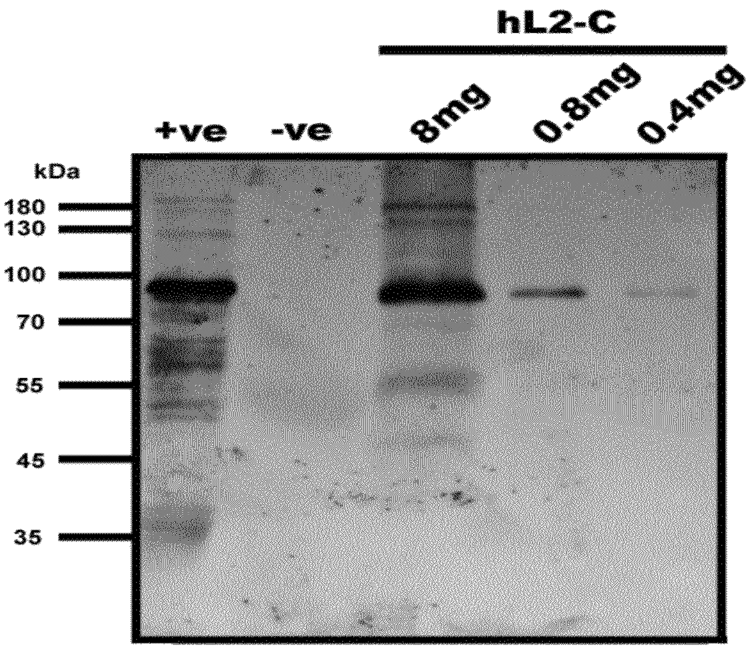

FIG. 16 shows a crude quantification of the amount of L2 present in leaf material after infiltration. *N. benthamiana* was infiltrated with the *Agrobacterium* strain containing the pTRA-hL2-C vector. Plant material was extracted four days after infiltration. Various amounts of leaf material (8 mg, 0.8 mg and 0.4 mg) were empirically determined and loaded onto a western. Westerns were probed using the rabbit pAb-αL2.

Figure 17:
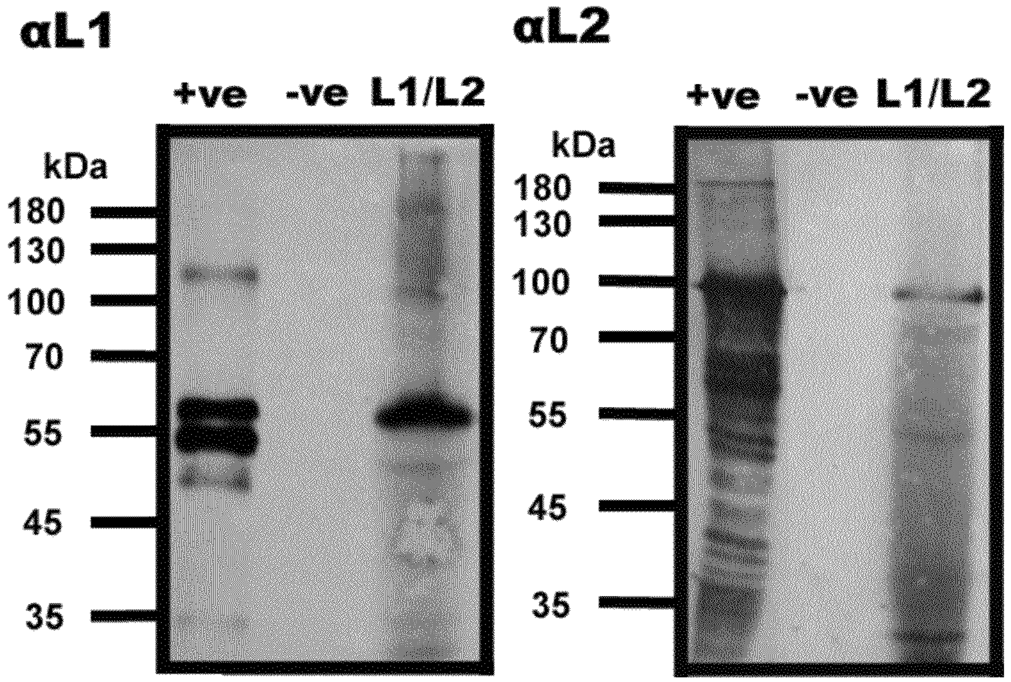

FIG. 17 shows L1 and L2 are co-expressed in the same region. *N. benthamiana* was infiltrated with the same OD of *Agrobacterium* containing the cytoplasmically-targeted humanised L1 gene mixed and co-infiltrated with *Agrobacterium* containing the humanised L2 gene in the vector also targeting the protein to the cytoplasm. Plant material that was co-infiltrated was extracted after four days and immunoblotted (L1/L2). Uninfiltrated plant material was used as a negative (−ve). *E. coli-expressed* L2 was loaded and run as a positive control. Immunoblots were either probed with mouse mAb J4 (αL1) or with rabbit polyclonal Ab-αL2 (αL2).

In this specification, where any sequence according to the invention is described or otherwise set out, the invention is intended to encompass sequences of at least 75% homology, more preferably at least 77% homology, even more preferably at least 80% homology, even more preferably at least 82% homology, even more preferably at least 85% homology, even more preferably at least 87% homology, even more preferably at least 90% homology, even more preferably at least 92% homology, even more preferably at least 95% homology, most preferably at least 97% homology, The following references are included herein by reference.

Kapila, J., De Rycke, R., Van Montagu, M., and Angenon, G. (1997). An *Agrobacterium*-mediated transient gene expression system for intact leaves. *Plant Science* 122, 101-108.

Pastrana, D. V., Buck, C. B., Pang, Y. Y., Thompson, C. D., Castle, P. E., FitzGerald, P. C., Kruger, K. S., Lowy, D. R., and Schiller, J. T. (2004). Reactivity of human sera in a sensitive, high-throughput pseudovirus-based papillomavirus neutralization assay for HPV16 and HPV18. Virology 321, 205-216.

Sambrook, J., Fritsch, E., and Maniatis, T. E. (1989). Molecular cloning, a laboratory manual. (Cold Spring Harbour Laboratory Press: Cold Spring Harbour, New York.)

Shen, W. J. and Forde, B. G. (1989). Efficient transformation of *Agrobacterium* spp. by high voltage electroporation. *Nucleic Acids Res.* 17, 8385.

Somers, D. A. and Makarevitch, I. (2004). Transgene integration in plants: poking or patching holes in promiscuous genomes? *Curr. Opin. Biotechnol.* 15, 126-131.

Studentsov, Y. Y., Schiffman, M., Strickler, H. D., Ho, G. Y., Pang, Y. Y., Schiller, J., Herrero, R., and Burk, R. D. (2002). Enhanced enzyme-linked immunosorbent assay for detection of antibodies to virus-like particles of human papillomavirus. *J. Clin. Microbiol.* 40, 1755-1760.

Takeda, A., Sugiyama, K., Nagano, H., Mori, M., Kaido, M., Mise, K., Tsuda, S., and Okuno, T. (2002). Identification of a novel RNA silencing suppressor, NSs protein of Tomato spotted wilt virus. *FEBS Lett.* 532, 75-79.

Twyman, R. M. (2004). Host Plants, Systems and Expression Strategies of Molecular Farming. In 'Molecular Farming'. (Eds. R. Fischer and S. Schillberg.) pp. 191-216. (Wiley-VCH Verlag GmbH & Co. KGaA: Weinheim.)

Voinnet, O. (2001). RNA silencing as a plant immune system against viruses. Trends Genet. 17, 449-459.

Voinnet, O., Rivas, S., Mestre, P., and Baulcombe, D. (2003). An enhanced transient expression system in plants based on suppression of gene silencing by the p19 protein of tomato bushy stunt virus. Plant J. 33, 949-956.

Zhou, J., Doorbar, J., Sun, X. Y., Crawford, L., Mclean, C. S., and Frazer, I. H. (1991). Identification of the Nuclear Localisation Signal of Human Papillomavirus Type 16 L1 Protein. Virology 185, 625-632.

Zupan, J., Muth, T. R., Draper, 0., and Zambryski, P. (2000). The transfer of DNA from *agrobacterium tumefaciens* into plants: a feast of fundamental insights. Plant J. 23, 11-28.

Pagny, S., P. Lerouge, L. Faye, and V. Gomord. 1999. Signals and mechanisms for protein retention in the endoplasmic reticulum. J. Exp. Bot. 50(331): 157-164

Cline, K. and R. Henry. Import and routing of nucleus-encoded chloroplast proteins. 1996. Annu. Rev. of Cell Dev. Biol. 12: 1-26

Nowak, W., M. Gawlowska, A. Jarmolowski, and J. Augustyniak. 2001. Effect of nuclear attachment regions on transgene expression in tobacco plants. Acta Biochim Pol. 48(3): 637-646

Rukatsova, E., O. Zolova, N. Buryanova, V. Borisova, V. Bykova, and Y. Burynova. 2003. Russ. J. Genet. 39(1): 41-45

Koncz, C. and J. Schell. 1986. The Promoter of $T_L$-DNA gene 5 controls the tissue-specific expression of chimaeric genes carried by a novel type of *Agrobacterium* binary vector. Mol. Gen. Genet. 204: 383-396

Vaquero, C., M. Sack, J. Chandler, J. Drossard, F. Schuster, M. Monecke, S. Schillberg, and R. Fischer. 1999. Transient expression of a tumor-specific single-chain fragment and a chimeric antibody in tobacco leaves. Proc. Natl. Acad. Sci. 96: 11128-11133

Biemelt, S., U. Sonnemald, P. Galmbacher, L. Willmitzer, and M. Müller. 2003. Production of Human Papillomavirus Type 16 Virus-Like Particles in Transgenic Plants. J. Virol. 77(17): 9211-9220

The invention claimed is:

1. A method of producing an influenza virus haemagglutinin 5(H5) polypeptide in a plant comprising the steps of:

cloning an influenza virus H5 gene or nucleic acid encoding a functional equivalent thereof into a vector containing a targeting sequence to target a polypeptide expressed in the cytoplasm to components present in the plant, wherein the plant components are selected from the group consisting of endoplasmic reticuli and apoplasts;

infiltrating at least a portion of the plant with the vector or transforming plant tissue with the vector so as to either transiently express the influenza virus H5 polypeptides in the cytoplasm and then import the influenza virus H5 polypeptides into the endoplasmic reticuli or apoplasts, and/or to create a transgenic plant wherein the influenza virus H5 polypeptides are expressed in the cytoplasm and then imported into the endoplasmic reticuli or apoplasts; and recovering the influenza virus H5 polypeptide expressed by the plant.

2. The method according to claim 1, wherein the targeting sequences encode a polypeptide for directing the influenza virus H5 polypeptide from the cytoplasm to the endoplasmic reticuli.

3. The method according claim 1, wherein the vector includes promoters and other regulators operably linked to the coding sequence of the vector.

4. The method according to claim 1, wherein the vector is a binary vector.

5. The method according to claim 1, wherein the influenza virus H5 gene is a codon optimized gene.

6. The method according to claim 1 further including a step of co-infiltration of the plant with a suppressor protein adapted to inhibit post-transcriptional gene silencing in the plant.

7. The method according to claim 1, wherein the infiltration is done by direct injection or by vacuum.

8. The method according to claim 1, wherein infiltration and/or transformation of the plant is achieved with *Agrobacterium tumefaciens* which has been transformed to accept the vector.

9. The method according to claim 1, wherein the plant is selected from *Nicotiana benthamiana* and *N. tabacum*.

10. The method according to claim 1, wherein the influenza virus H5 gene or nucleic acid encoding a functional equivalent thereof is selected from SEQ ID NOS: 15 or 16.

11. The method according to claim 1, wherein infiltration is performed upon the leaves of the plant.

12. The method according to claim 1, wherein substantially the whole plant is infiltrated with a suitable vector by means of vacuum infiltration.

13. The method according to claim 1, wherein the infiltration is by direct injection infiltration and is performed on the abaxial region of the leaf.

14. The method according to claim 1, wherein the influenza virus H5 gene is modified to remove its membrane anchoring domain.

15. The method according to claim 6, wherein the suppressor protein is the NSs protein of the tomato spotted wilt virus or the p19 of tomato bushy stunt virus.

16. The method according to claim 5, wherein the optimized gene is human-codon optimized, BCG-codon optimized or plant-codon optimized.

17. The method according to claim 4, wherein the vector is *Agrobacterium tumefaciens* binary vector.

18. The method according to claim 1, wherein the influenza virus H5 polypeptides are selected from the group consisting of a influenza virus H5 protein; a chimaeric influenza virus H5 peptide fused to another influenza antigen; and a chimaeric influenza virus H5 fused to a heterologous peptide derived from any antigenic epitope, B-cell or T-cell specific.

* * * * *